(12) United States Patent
Yang et al.

(10) Patent No.: US 9,040,102 B2
(45) Date of Patent: May 26, 2015

(54) **COMPOSITION COMPRISING *LONGAN ARILLUS* EXTRACT OR COMBINED EXTRACT COMPRISING THE SAME FOR TREATING NEURODEGENERATIVE DISEASE**

(75) Inventors: Hyun-Ok Yang, Seoul (KR); Na-Young Bae, Cheonan-si (KR); Hak-Cheol Kwon, Seoul (KR); Sung-Kwon Chung, Seoul (KR); Myung-Sook Oh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 223 days.

(21) Appl. No.: 13/031,751

(22) Filed: Feb. 22, 2011

(65) Prior Publication Data

US 2011/0318435 A1 Dec. 29, 2011

(30) Foreign Application Priority Data

Jun. 24, 2010 (KR) ........................ 10-2010-0060181

(51) Int. Cl.
| | | |
|---|---|---|
| *A61K 36/539* | (2006.01) | |
| *A61K 36/00* | (2006.01) | |
| *A61K 36/48* | (2006.01) | |
| *A61K 36/31* | (2006.01) | |
| *A61K 36/77* | (2006.01) | |
| *A61K 36/488* | (2006.01) | |

(52) U.S. Cl.
CPC ................. *A61K 36/77* (2013.01); *A61K 36/31* (2013.01); *A61K 36/488* (2013.01); *A61K 36/539* (2013.01)

(58) Field of Classification Search
None
See application file for complete search history.

(56) References Cited

FOREIGN PATENT DOCUMENTS

| | | | |
|---|---|---|---|
| CN | 1799620 | | 7/2006 |
| JP | 05-139982 | | 6/1993 |
| JP | 2003-113117 | | 4/2003 |
| JP | 2005-501018 | | 1/2005 |
| JP | 2007-230938 | | 9/2007 |
| JP | 2007230938 A | * | 9/2007 |
| KR | 2001100549 A | * | 11/2001 |
| KR | 2003079105 A | * | 10/2003 |
| WO | 2007-004390 | | 1/2007 |

OTHER PUBLICATIONS

Howes, et al. (2003) Phytother. Res. 17, pp. 1-18.*
Lin et al. (2008) Chemico-Biological Interactions, 175 pp. 352-354.*
Lu et al. (2006) Neurochemistry Inter 48; pp. 263-274.*
Ma et al. (2009) J. Ethnopharmacology 122: pp. 245-250.*
Ono et al. (2003) J. Neurochemistry 87: pp. 172-181.*
Park et al. (2010) J. Ethnopharmacology 128: pp. 160-165.*
Porat et al. (2006) Chem. Biol. Drug Des 67: pp. 27-37.*
Rangkadilok et al. (2005) J. Agric. Food Chem. 53, pp. 1387-1392.*
Yabe et al. (2003) Phytomedicine 10: pp. 106-114.*
Zhang et al. (2008) Cell Biology Inter. 32: pp. 1230-1237.*
Park et al. (2010) J. Ethnopharmacology 128: 160-165.*
Bae, Na-Young, Ph. D. Thesis, Neuroprotective effect of modified Yeoldahanso-tang via autophagy enhancement on Parkinsonian model, 2, 2010, pp. 98-100.
Unabridged Dictionary of Chinese Medication, first edition vol. 4, pp. 2680-2681, (1985).

* cited by examiner

*Primary Examiner* — Chris R Tate
*Assistant Examiner* — Russell Fiebig
(74) *Attorney, Agent, or Firm* — Lexyoume IP Meister, PLLC

(57) ABSTRACT

This disclosure relates to a composition for prevention or treatment of neurodegenerative disease comprising longan arillus extract, or combined extract comprising longan arillus. The composition exhibits remarkably excellent prevention or treatment effect of neurodegenerative disease by containing longan arillus extract or combined extract comprising longan arillus, and particularly, it may effectively prevent or treat neurodegenerative disease by significantly protecting dopaminergic neurons from neurotoxicity due to MPTP selectively acting on dopaminergic nervous system and neurotoxicity due to aggregation of alpha-synuclein proteins.

4 Claims, 16 Drawing Sheets

COMPOSITION COMPRISING *LONGAN ARILLUS* EXTRACT OR COMBINED EXTRACT COMPRISING THE SAME FOR TREATING NEURODEGENERATIVE DISEASE

CROSS-REFERENCE TO RELATED APPLICATION

This application claims priority to and the benefit of Korean Patent Application No. 10-2010-0060181 filed on Jun. 24, 2010, and Patent Application No. 2010-249044 filed on Nov. 5, 2010, the entire contents of which are incorporated herein by reference.

BACKGROUND OF THE INVENTION (a) Field of the Invention

The present invention relates to a composition for prevention or treatment of neurodegenerative disease comprising longan arillus extract, or combined extract comprising the same, more particularly to a pharmaceutical composition or a food composition for prevention or treatment of neurodegenerative disease comprising the extract as an active ingredient.

(b) Description of the Related Art

A neurodegenerative disease primarily represented by Parkinson's Disease is characterized by dopaminergic neuron death in substantia nigra pars compacta. The decrease of dopamine, a neurotransmitter in striatum adversely affects the balance of neurotransmission system, thus showing representative symptoms of Parkinson's Disease including tremor, rigidity, bradykinesia, and postural instability, etc.

However, the pathological cause of neurodegenerative disease such as Parkinson's Disease has not been clarified. It has been limitedly hypothesized that loss of dopaminergic neurons may be caused by genetic factors or external toxicity, etc., and recent studies have reported that cerebral arteriosclerosis, carbon monoxide-poisoning, drugs, metabolic diseases caused by hypoparathyroidism, and traumatic encephalitis sequelae may have some connections therewith.

Although effective therapies for neurodegenerative disease have been scarcely developed until 1970's, supplementing a dopamine decrease in brain tissue using dopamine precursor L-dopa, or a therapy using dopamine receptor agonist including anticholinergic drug, for example Eldepryl has been currently known. However, most of these drugs focus on only controlling symptoms rather than treating underlying cause, and a long term administration of these drugs may cause side-effects. For example, since anticholinergic drugs may cause abnormalities in autonomic nervous system or mental function, there is a limit in continuously administering to an elderly patient. In addition, a long term use of L-dopa medication shows a gradual decrease in its effectiveness and also causes side effects, e.g., abnormal movements such as body twist and involuntary movement of hands and feet. Surgical therapies such as a nerve stimulation using high frequency, i.e., radiofrequency ablation or deep brain stimulation, etc. have been performed, but it may require an invasive surgical procedure and high costs.

Accordingly, although the development of symptomatic treatment for improving clinical symptoms is important in the treatment of neurodegenerative disease such as Parkinson's Disease, the development of causative treatment for preventing death of dopaminergic neurons in substantia nigra, which is a direct cause of Parkinson's Disease, is urgently required.

According to recent studies on the cause of neurodegenerative disease such as Parkinson's Disease, a protein called alpha-synuclein has been found in the brain of a patient suffering from Parkinson's Disease in an abnormally folded form. The accumulation of alpha-synuclein in cells, leading to destruction of neurons is known to be one of characteristics of Parkinson's Disease. Thus, studies on the method of dissolving or preventing aggregation of such abnormal proteins have attracted much attention as a novel therapy for preventing or delaying the progression of Parkinson's Disease. (Ryu, J. et al. Quality evolution and components of Euphoria longana. Kor. J. Pharmacogn. 33; 191~193, 2002)

Meanwhile, Ubiquitin-proteasome system (UPS) is a representative proteolysis mechanism occurring in human body, and it is known that in many patients with neurodegenerative disease, such function is attenuated and thus accumulation of modified proteins cannot be controlled (Olanow C. W, McNaught K. S. Ubiquitin-proteasome system and Parkinson's disease. Mov. Disord. 2006; 21:1806-1823). In addition to UPS, an important proteolysis mechanism includes Autophagy-lysosomal pathway (ALP), which has been recently studied as an important target for treatment of neurodegenerative diseases (Bandhyopadhyay U, Cuervo A M. Chaperone-mediated autophagy in aging and neurodegeneration: lessons from alpha-synuclein. Exp Gerontol. 2007; 42:120-8). Specifically, if the function of UPS becomes abnormal and decomposition of lysosome is blocked, another proteolysis pathway called autophagy is activated as a way of compensation. In this mechanism, abnormal proteins such as alpha-synuclein are decomposed and proteins are accumulated in brain neurons to prevent cell damage (Martinez-Vicente M. Cuervo A. M, Autophagy and neurodegeneration: when the cleaning crew goes on strike. Lancet Neurol. 2007; 6:352-361, Ravikumar B, Duden R, Rubinsztein D. C. Aggregate-prone proteins with polyglutamine and polyalanine expansions are degraded by autophagy. Hum Mol. Genet. 2002; 11:1107-1117). Therefore, it is important to develop a therapy through ALP, i.e. autophagy in patients with neurodegenerative disease having abnormal UPS function.

SUMMARY OF THE INVENTION

While studying on natural materials having neurodegenerative disease preventing and treating effects, the present inventors have found that longan arillus extract and combined extract comprising the same are very effective for prevention and treatment of neurodegenerative disease and completed the invention.

Accordingly, one embodiment of the present invention relates to a pharmaceutical composition for prevention, improvement or treatment of neurodegenerative disease comprising longan arillus extract as an active ingredient.

Another embodiment relates to a method for prevention, improvement, or treatment of neurodegenerative disease comprising administering a composition comprising longan arillus extract as an active ingredient to a patient in need of prevention, improvement or treatment of neurodegenerative disease.

Yet another embodiment relates to food for prevention or improvement of neurodegenerative disease comprising longan arillus extract, and a method for preparing the same.

DETAILED DESCRIPTION OF THE EMBODIMENTS

To solve the above problems, it is an object of the present invention to provide a method for treating, preventing or improving neurodegenerative disease comprising administering a composition comprising longan arillus extract as an active ingredient to a patient in need of prevention or treatment of neurodegenerative disease.

It is another object of the present invention to provide food for preventing or improving neurodegenerative disease comprising longan arillus extract, and a method for preparing the same.

Hereinafter, the present invention will be explained in detail

One embodiment provides a pharmaceutical composition for preventing, treating or improving neurodegenerative disease comprising longan arillus extract as an active ingredient. Another embodiment provides a method for preventing, improving or treating neurodegenerative disease comprising administering a composition comprising longan arillus extract as an active ingredient to a patient in need of prevention, improvement or treatment of neurodegenerative disease. The method for preventing, improving or treating neurodegenerative disease may further comprise identifying a patient in need of prevention, improvement or treatment of neurodegenerative disease prior to the administration. The patient may be mammals including human.

According to one embodiment, the composition may comprise longan arillus extract alone. According to another embodiment, the composition may further comprise at least one extract selected from the group consisting of Angelicae tenuissimae radix and Polygalae radix. According to yet another embodiment, the composition may further comprise at least one extract selected from the group consisting of Puerariae radix, Scutellaria radix, Platycodi radix, Angelicae Dahuricae radix, Cimicifugae Rhizoma, Raphani Semen, and Acorus Graminer. For example, the composition may comprise 1) longan arillus extract alone, 2) combined extract of i) longan arillus, and ii) at least one of Polygalae radix and Angelicae tenuissimae radix, or 3) combined extract of i) longan arillus, ii) at least one of Angelicae tenuissimae radix and Polygala tenuifolia, and iii) at least one selected from Puerariae Radix, Scutellaria radix, Platycodi Radix, Angelicae Dahuricae Radix, Cimicifugae Rhizoma, Raphani Semen, and Acorus Gramineri Rhizoma.

The term 'combined extract' used herein includes both a mixture of extracts separately extracted from each of herbal medicine material, as well as extract of a mixture of herbal medicine materials obtained by mixing herbal medicine materials and extracting. And, the ratio of each herbal medicine ingredient in combined extract refers to the ratio of each extract of herbal medicine material for a mixture of extracts, and the ratio of each herbal medicine in a mixture of herbal medicine materials for extract of a mixture The term 'longan arillus' used herein refers to aril of longan tree belonging to Sapindaceae, and its herbal medicine name is longan arillus or longanae arillus.

The term 'Angelicae tenuissimae radix' used herein refers to a medicinal plant belonging to Apiaceae, and its herbal medicine name is angelicae tenuissimae radix. In the present invention, roots, stems and leaves of the plant may be extracted, and preferably roots of the plant may be used.

The term 'Polygalae radix' used herein refers to a medicinal plant belonging to Polygalaceae, and its herbal medicine name is polygalae radix. In the present invention, roots, stems and leaves of the plant may be extracted, and preferably roots of the plant may be used.

The term 'Puerariae radix' used herein refers to periderm-removed root of Pueraria lobata (Willd.) Ohwi.

The term 'Scutellaria radix' used herein refers to a perennial plant belonging to the class of Dicotyledoneae, order of Tubiflorales, family of Labiatae, and in the present invention, roots, stems and leaves of the plant may be extracted, and preferably roots of the plant may be used.

The term 'Platycodi Radix' used herein refers to a perennial plant belonging to Campanulaceae, and it blooms white and purple flowers in the summer. In the present invention, roots, stems and leaves of the plant may be extracted, and preferably roots of the plant may be used.

The term 'Cimicifugae Rhizoma' used herein refers to a medicine made of rhizome of Cimicifugae Rhizoma Komarov belonging to Ranunculaceae or plants of the same genus.

The term 'Angelicae Dahuricae Radix' used herein refers to a medicine made by drying the root of Angelicae Dahuricae Radix Bentham et Hooker belonging to Umbelliferae or a variety thereof.

The term 'Raphani Semen' used herein refers to a medicine made using seeds of Raphanus sativus L. belonging to Cruciferae or plants of the same genus.

The term 'Acorus Gramineri Rhizoma' used herein refers to a perennial plant belonging to class of Monocotyledoneae, order of Arales, family of Araceae. In the present invention, roots, stems and leaves of the plant may be extracted, and preferably roots of the plant may be used.

The term 'neurodegenerative disease' used herein, although not limited thereto, may be preferably Alzheimer's disease, Parkinson's Disease, Amyotrophic Lateral Sclerosis (Lou Gehrig's disease) or Multiple sclerosis, most preferably Parkinson's Disease.

The extract may be hot-water extract or organic solvent extract, and it may be prepared by any plant extract preparation method known in the art.

The extraction solvent used for preparation of longan arillus extract and combined extract may be at least one selected from the group consisting of water, at least one organic solvent selected from C1-4 lower alcohol, hexane, methylene chloride, acetonitrile and acetone, and a mixed solvent thereof.

More specifically, the longan arillus extract may be primary extract obtained by using at least one selected from water and C1-4 lower alcohol; secondary extract obtained by further extracting the primary extract using at least one selected from water, hexane, methylene chloride and $C_{1-4}$ lower alcohol; or tertiary extract obtained by further extracting the secondary extract using at least one selected from acetonitrile, methanol, acetone and water.

The extract of a mixture of herbal medicine materials may be primary extract obtained by extracting a mixture of longan arillus and at least one of Angelicae tenuissimae radix and Polygalae radix, or a mixture of longan arillus, at least one of Angelicae tenuissimae radix and Polygalae radix, and at least one selected from Puerariae Radix, Scutellaria radix, Platycodi Radix, Angelicae Dahuricae Radix, Cimicifugae Rhizoma, Raphani Semen and Acorus Gramineri Rhizoma using at least one selected from water and C1-4 lower alcohol; secondary extract obtained by further extracting the primary extract using at least one selected from water, hexane, methylene chloride and C1-4 lower alcohol; or tertiary extract obtained by extracting the secondary extract using at least one selected from acetonitrile, methanol, acetone and water.

In the mixture of each herbal medicine extract, each herbal medicine extract may be primary extract obtained by extracting each herbal medicine material using at least one selected from water and C1-4 lower alcohol; secondary extract obtained by further extracting the primary extract using at least one selected from water, hexane, methylene chloride and C1-4 lower alcohol; or tertiary extract obtained by further extracting the secondary extract using at least one selected from acetonitrile, methanol, acetone and water.

One experiment uses hot-water extract prepared by adding water to longan arillus extract or combined extract comprising the same (see <Example 1>).

The active ingredient having the activity of prevention or treatment of neurodegenerative disease may be longan arillus extract alone (YA), preferably combined extract of longan arillus and at least one of Angelicae tenuissimae radix and Polygalae radix, or combined extract of longan arillus, at least one of Angelicae tenuissimae radix and Polygalae radix, and at least one selected from Puerariae Radix, Scutellaria radix, Platycodi Radix, Angelicae Dahuricae Radix, Cimicifugae Rhizoma, Raphani Semen and Acorus Gramineri Rhizoma. More preferably, combined extract (DG) of longan arillus, Angelicae tenuissimae radix and Polygalae radix, more preferably combined mixture (MYH) of longan arillus, Angelicae tenuissimae, Polygalae radix Puerariae Radix, Scutellaria radix, Platycodi Radix, Angelicae Dahuricae Radix, Cimicifugae Rhizoma, Raphani Semen and Acorus Gramineri Rhizoma may be used.

If the extract is combined extract of longan arillus and Polygalae radix, the longan arillus and Polygalae radix may be combined and extracted at the weight ratio of 1:0.2 to 1:10, preferably 1:0.4 to 1:5, more preferably 1:0.8 to 1:2.5, and most preferably, the longan arillus and Polygalae radix may be combined and extracted at the weight ratio of 1:1.

If the extract is combined extract of longan arillus and Angelicae tenuissimae radix, the longan arillus and Angelicae tenuissimae radix may be combined and extracted at the weight ratio of 1:0.1 to 1:5, preferably 1:0.2 to 1:2.5, more preferably 1:0.8 to 1:1.25, and most preferably, the longan arillus and Angelicae tenuissimae radix may be combined and extracted at the weight ratio of 1:1.

If the extract is combined extract of longan arillus, Polygalae radix and Angelicae tenuissimae radix, the longan arillus, Polygalae radix and Angelicae tenuissimae radix may be combined and extracted at the weight ratio of 1:0.1 to 10:0.1 to 10, preferably 1:0.2 to 5:0.2 to 5, more preferably 1:0.4 to 2.5:0.4 to 2.5, and most preferably, 1:1:1 (the combined extract is indicated as 'DG').

If the extract is combined extract of longan arillus, Polygalae radix, Angelicae tenuissimae radix, Puerariae Radix, Scutellaria radix, Platycodi Radix, Angelicae Dahuricae Radix, Cimicifugae Rhizoma, Raphani Semen and Acorus Gramineri Rhizoma, although not limited thereto, 15 to 20 parts by weight of longan arillus, 10 to 15 parts by weight of Angelicae tenuissimae radix, 10 to 15 parts by weight of Polygalae radix, 15 to 20 parts by weight of Puerariae Radix, 5 to 10 parts by weight of Scutellaria radix, 1 to 5 parts by weight of Platycodi Radix, 5 to 10 parts by weight of Angelicae Dahuricae Radix, 5 to 10 parts by weight of Cimicifugae Rhizoma, 5 to 10 parts by weight of Raphani Semen and 15 to 20 parts by weight of Acorus Gramineri Rhizoma may be combined and extracted, preferably 15 to 18 parts by weight of longan arillus, 10 to 13 parts by weight of Angelicae tenuissimae radix, 10 to 13 parts by weight of Polygalae radix, 15 to 18 parts by weight of Puerariae Radix, 5 to 8 parts by weight of Scutellaria radix, 1 to 3 parts by weight of Platycodi Radix, 5 to 8 parts by weight of Angelicae Dahuricae Radix, 5 to 8 parts by weight of Cimicifugae Rhizoma, 5 to 8 parts by weight of Raphani Semen and 15 to 18 parts by weight of Acorus Gramineri Rhizoma may be combined and extracted, and most preferably 16 to 18 parts by weight of longan arillus, 10 to 12 parts by weight of Angelicae tenuissimae radix, 10 to 12 parts by weight of Polygalae radix, 16 to 18 parts by weight of Puerariae Radix, 5 to 7 parts by weight of Scutellaria radix, 2 to 3 parts by weight of Platycodi Radix, 5 to 7 parts by weight of Angelicae Dahuricae Radix, 5 to 7 parts by weight of Cimicifugae Rhizoma, 5 to 7 parts by weight of Raphani Semen and 16 to 18 parts by weight of Acorus Gramineri Rhizoma may be combined and extracted.

According to one example, in order to analyze the effect of longan arillus extract or combined extract comprising longan arillus on brain cell death, brain cell death is induced by MPTP (see <Example 2>) and the extract is administered, and as the result, it can be seen that the extracts have the activities for effectively inhibiting brain cell death and thus have brain cell protection effects.

According to one example, it can be seen that longan arillus extract or combined extract comprising longan arillus has excellent effect for inducing autophagy which promotes decomposition of alpha-synuclein protein known as a cause of Parkinson's Disease (see <Example 3>).

According to one example (in vivo experiment), Parkinson's Disease is induced by MPTP in a mouse, and then, Pole test, Rota-rod test and dopaminergic neuron protection activity test are conducted. As results, it can be seen that when longan arillus extract or combined extract comprising longan arillus is administered, degeneration of motor function caused by MPTP is restored (see <Example 4>), and excellent dopaminergic neuron protection activity is shown in striatum and substantia nigra (see <Example 4>). Furthermore, it can be seen that brain cell death caused by MPTP can also be effectively inhibited by Tyrosine hydroxylase immunohistochemistry (TH-IHC) and TH-IR (immunoreactivity) using avidin-biotin peroxidase (see <Example 4>).

Therefore, the pharmaceutical composition of the present invention has remarkably excellent effects for prevention or treatment of neurodegenerative disease, by comprising longan arillus extract alone, preferably combined extract of longan arillus and at least one of Angelicae tenuissimae radix and Polygalae Radix, more preferably combined extract of longan arillus, at least one of Angelicae tenuissimae radix and Polygalae Radix, at least one selected from Puerariae Radix, Scutellaria radix, Platycodi Radix, Angelicae Dahuricae Radix, Cimicifugae Rhizoma, Raphani Semen and Acorus Gramineri Rhizoma as an active ingredient.

More specifically, the pharmaceutical composition of the present invention may prevent or treat neurodegenerative disease by significantly protecting dopaminergic neurons from neurotoxicity triggered by MPTP selectively acting on dopaminergic nervous system or by alpha-synuclein protein aggregation.

The content of the extract as an active ingredient in the pharmaceutical composition may be appropriately controlled depending on the form and purpose of use, condition of patient, kind and severance of symptoms, etc., and it may be 0.001 to 99.9 wt %, preferably 0.1 to 50 wt %, based on solid content weight, but not limited thereto. The "solid content weight" refers to the weight of remaining ingredients after removing a solvent in the extract.

The pharmaceutical composition of the present invention may be administered to mammals including human by various routes. It may be administered by any commonly used administration method, for example, by oral, rectal, intravenous, intramuscular, subcutaneous, intrauterine or intracerebroventricular injection. The pharmaceutical composition of the present invention may be formulated into an oral dosage form such as powder, granule, a tablet, a capsule, suspension, emulsion, syrup, aerol, etc., or a parenteral dosage form such as an epidermal formulation, suppositories and an sterilized injection solution, etc.

The pharmaceutical composition of the present invention may further comprise pharmaceutically appropriate and physiologically acceptable adjuvant such as carrier, diluents or excipient. The carrier, excipient and diluents that may be comprised in the pharmaceutical composition of the present invention may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil. And, for formulation, diluents or excipient such as a filler, a bulking agent, a binder, a wetting agent, a disintegrating agent, surfactant, etc. may be used. A solid formulation for oral administration may include a tablet, a pill, powder, granule, a capsule, etc., and it may be prepared by mixing the extract of Polygalae Radix, Angelicae tenuissimae radix and longan arillus with at least one excipient, for example, starch, calcium carbonate, sucrose or lactose, gelatin, etc. In addition to simple excipient, a lubricant such as magnesium stearate, talc may be used. A liquid formulation for oral administration may include suspension, oral liquid preparation, emulsion, syrup, etc., and, it may comprise various excipients such as a wetting agent, a flavoring agent, a sweetening agent, a preservation agent, etc. in addition to commonly used simple diluents such as water and liquid paraffin. A formulation for parenteral administration may include a sterilized aqueous solution, suspension, emulsion, a freeze dried formulation, suppositories, an epidermal formulation, etc. The non-aqueous liquid preparation, suspension may include vegetable oil such as propylene glycol, polyethyleneglycol, or olive oil, and injectable ester such as ethyl oleate. The suppository base may include witepsol, macrogol, tween 61, cacao butter, laurinum, glycerogelatin, etc.

Although the pharmaceutical composition of the present invention may be administered alone to human, it may be generally administered with pharmaceutical carrier selected considering administration route and standard pharmaceutical practice. For example, the pharmaceutical composition of the present invention may be administered orally, in an oral cavity or sublingually in a tablet form containing starch or lactose, or in a capsule form with or without excipient, or in an elixir or suspension form containing sweetening or coloring chemical drugs. The liquid base may be formulated with pharmaceutically acceptable additives such as suspension (for example, semisynthesized glyceride such as methylcellulose, witepsol, or a glyceride mixture such as a mixture of apricot kernel oil and PEG-6 ester or a mixture of PEG8 and caprylc/capric glyceride).

The dosage amount of the pharmaceutical composition of the present invention may vary depending on the age, body weight, gender of patient, administration form, health condition and severance of disease, and it may be divisionally administered at a regular interval once to a several times a day. For example, a one day dose may be 0.5 to 50 mg/kg, preferably 1 to 30 mg/kg, based on the content of active ingredient. The above described dose is an illustration of the average, and dose may be higher or lower depending on personal difference. If a single day dosage of the pharmaceutical composition of the present invention is less than the above range, significant effect may not be obtained, and if it exceeds the above range, it may be uneconomical and it may cause undesirable side-effects because it does not fall within commonly used amount.

The patient refers to mammals including human who is diagnosed with neurodegenerative disease, preferably Parkinson's Disease, or in need of prevention, improvement and/or treatment of the disease.

Meanwhile, the food for prevention or improvement of neurodegenerative disease may comprise longan arillus extract alone, preferably combined extract of longan arillus and at least one of Angelicae tenuissimae radix and Polygalae radix, more preferably combined extract of longan arillus, at least one of Angelicae tenuissimae radix and Polygalae radix, and at least one selected from Puerariae Radix, Scutellaria radix, Platycodi Radix, Angelicae Dahuricae Radix, Cimicifugae Rhizoma, Raphani Semen and Acorus Gramineri Rhizoma.

According to another embodiment, provided is a method for preparing food for preventing or improving neurodegenerative disease comprising preparing the following extract using at least one extraction solvent selected from the group consisting of water, at least one organic solvent selected from C1-4 lower alcohol, hexane, methylene chloride, acetonitrile and acetone, and a mixed solvent thereof: 1) longan arillus extract; 2) combined extract of i) longan arillus, and ii) at least one of Angelicae tenuissimae radix and Polygalae radix, or 3) combined extract of i) longan arillus, ii) at least one of Angelicae tenuissimae radix and Polygalae radix, and iii) at least one selected from Puerariae Radix, Scutellaria radix, Platycodi Radix, Angelicae Dahuricae Radix, Cimicifugae Rhizoma, Raphani Semen and Acorus Gramineri Rhizoma; and preparing food using the above prepared extract.

The extraction solvent and the preparation method of the extract, and the activities for prevention and/or improvement of neurodegenerative disease of the extract are as described above.

The food of the present invention may include all types of food such as functional food, nutritional supplement, health food and food additives. The above types of food may be prepared in various forms by common methods known in the art.

For example, for the health food, the longan arillus extract or combined extract may be prepared in the form of tea, juice and drink for drinking purpose, or it may be granulized, encapsulated or pulverized for digestion. And, any active ingredients known to have neurodegenerative disease improvement effect may be mixed with the longan arillus extract or combined extract, and prepared in the form of a composition.

And, the functional food may be prepared by adding the longan arillus extract or combined extract to beverage (including alcoholic beverage), fruit and processed food thereof (e.g., canned fruit, bottled food, jam, marmalade, etc.), fish, meat and processed food thereof (e.g., ham, sausage, corn beef, etc.), bread and noodles (e.g., udon, buckwheat noodles, ramen, spaghetti, macaroni, etc.), fruit juice, various drinks, cookies, taffy, milk products (e.g., butter, cheese, etc.), edible plant oil and butter, margarine, vegetable proteins, a retortable pouch, frozen food, various seasonings (e.g., soybean, soy sauce, etc.) and the like.

And, in order to use the longan arillus extract or combined extract in the form of food additives, it may be prepared in the form of powder or concentrate.

The longan arillus extract or combined extract may be preferably comprised in the food composition of the present invention in an amount of about 0.001 g to 20 g per 100 g food. Preferably, the longan arillus extract or combined extract may be mixed with any active ingredients known to have neurodegenerative disease improvement effect and prepared in the form of health food.

The composition of the present invention has remarkably excellent effects for preventing or treating neurodegenerative disease, by comprising longan arillus extract or combined extract comprising the same, and particularly, it may significantly protect dopaminergic neurons from neurotoxicity triggered by MPTP selectively acting on dopaminergic nervous system or by aggregation of alpha-synuclein proteins thereby effectively preventing or treating neurodegenerative disease.

EXAMPLE

Figure 1A:
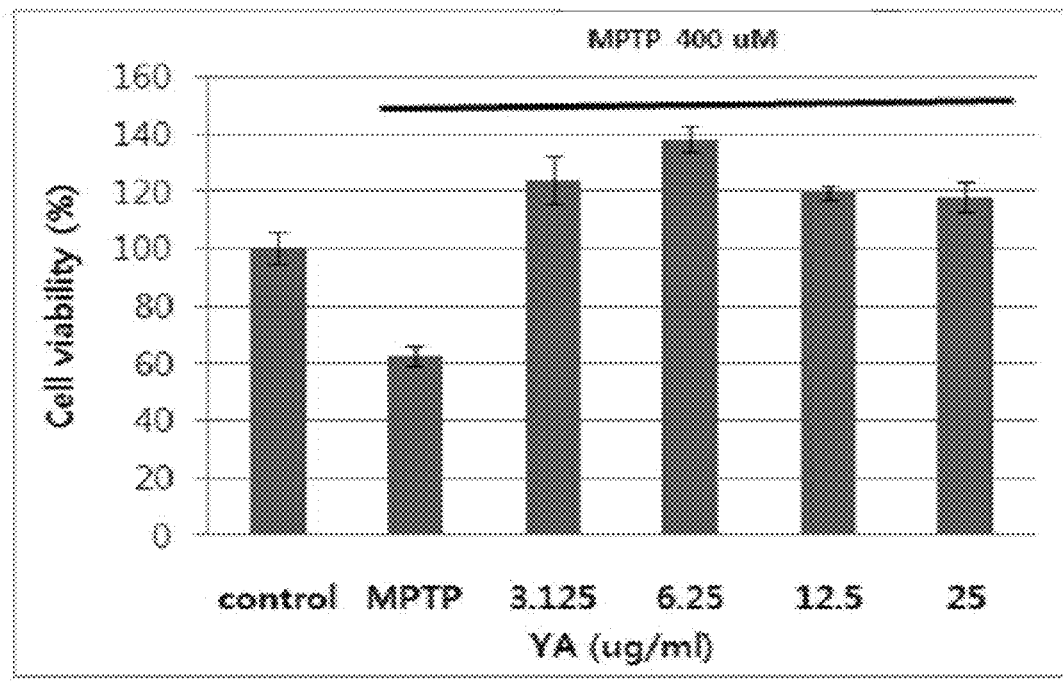
FIG. 1a shows the results of measurements of the effects of longan arillus extract on brain cell death caused by MPTP with increasing concentration (YA:longan arillus).

The present invention is further explained in more detail with reference to the following examples. These examples, however, should not be interpreted as limiting the scope of the present invention in any manner.

Example 1

Preparation of Longan Arillus Extract and Combined Extract Comprising Longan Arillus <1-1> Preparation of Longan Arillus Extract 40 g of longan arillus (Oriental Hospital of DAEJEON UNIVERSITY) was thoroughly washed and cut into small pieces, and then, water was added thereto in an amount of 4 times of the weight to primarily extract at 95° C. for 4 hours in a pottery extracting apparatus for decoction, and then, filtered and water was added again to the remaining solid content in the half amount to secondarily extract under the same conditions as the primary extraction.

The two extracts were collected and filtered to remove solid contents, and then, centrifuged at 3200 rpm for 20 minutes to collect the supernatant. The supernatant was filtered again using a 2.0 um microfilter and only liquid was collected and used.

<1-2> Preparation of Combined Extracts of Longan Arillus, Angelicae Tenuissimae Radix and Polygalae Radix with Various Mixing Ratios.

Combined extract of longan arillus and Angelicae tenuissimae radix, or longan arillus and Polygalae radix and combined extract of longan arillus, Angelicae tenuissimae radix and Polygalae radix were composed with various mixing ratios to prepare combined extracts by the same method as described in <Example 1-1>. All the raw materials of medicine were purchased from Oriental Hospital of DAEJEON UNIVERSITY.

Particularly, combined extract of longan arillus, Angelicae tenuissimae radix and Polygalae radix in the ratio of 1:1:1 is referred to as DG.

(1-methyl-4-phenyl-1,2,3,6-tetrahydropyridine) were identified as follows. Specifically, N-methyl-4-phenyl-1,2,3,6-tetrahydropyridine(MPTP) which selectively shows toxicity on dopaminergic nervous system was used to induce cytotoxicity on SH-SY5Y cell line and subsequently cell protection activity test was conducted.

<2-1> Medium Containing the Extract

The single extract or combined extract of <Example 1> was diluted in MEM medium containing 10% fetal bovine serum and 1% antibiotics (Gibco, Invitrogen, Carlsbad, Calif.) at a various concentrations and subsequently utilized.

TABLE 1

| 2 kinds-combined extract | | 3 kinds-combined extract | |
| --- | --- | --- | --- |
| name | Mixing ratio | name | Mixing ratio |
| Y1W1 | longan arillus 30 g:Polygalae radix 30 g | Y1W2G1 | longan arillus 15 g:Polygalae radix 30 g:Angelicae tenuissimae radix 15 g |
| Y1G1 | longan arillus 30 g:Angelicae tenuissimae radix 30 g | Y1W1G2 | longan arillus 15 g:Polygalae radix15:Angelicae tenuissimae radix 30 g |
| Y1W2 | longan arillus 20 g:Polygalae radix 40 g | Y1W2G2 | longan arillus 12 g:Polygalae radix 24 g:Angelicae tenuissimae radix 24 g |
| Y1G2 | longan arillus 20 g:Angelicae tenuissimae radix 40 g | Y1W1G1 (DG) | longan arillus 20 g:Polygalae radix 20 g:Angelicae tenuissimae radix 20 g |
| Y2W1 | longan arillus 40 g:Polygalae radix 20 g | Y2W1G1 | longan arillus 30 g:Polygalae radix 15 g:Angelicae tenuissimae radix 15 g |
| Y2G1 | longan arillus 40 g:Angelicae tenuissimae radix 20 g | Y2W2G1 | longan arillus 24 g:Polygalae radix 24 g:Angelicae tenuissimae radix 12 g |
| | | Y2W1G2 | longan arillus 24 g:Polygalae radix 12 g:Angelicae tenuissimae radix 24 g |

<1-3> Preparation of Combined Extract of Longan Arillus, Puerariae Radix, Angelicae Tenuissimae Radix, Scutellaria Radix, Platycodi Radix, Angelicae Dahuricae Radix, Cimicifugae Rhizoma, Raphani Semen, Polygalae Radix and Acorus Gramineri Rhizoma (MYH)

12 g of Puerariae Radix, 8 g of Angelicae tenuissimae radix, 4 g of Scutellaria radix, 2 g of Platycodi Radix, 4 g of Angelicae Dahuricae Radix, 4 g of Cimicifugae Rhizoma, 4 g of Raphani Semen, 8 g of Polygalae radix, 12 g of Acorus Gramineri Rhizoma, and 12 g of longan arillus were purchased from Oriental Hospital of DAEJEON UNIVERSITY, and combined extract was prepared by the same method as described in <Example 1-1>.

<2-2> Cell Culture

As a neuron model, SH-SY5Y cell (Accession No.: ATCC CRL-2266) originated from human neuron species was selected. The cells were cultured in MEM medium containing 10% fetal bovine serum and 1% antibiotics of <Example 2-1>.

<2-3> Cytotoxicity Test MTT Analysis

To measure the effects of longan arillus extract and combined extract (DG) and combined extract (MYH) of the present invention on viability of SH-SY5Y cell against cytotoxicity induced by 400 μM MPTP, a cytotoxicity measurement method that is well known in the field (MTT Cell Proliferation assay) was used.

TABLE 2

| Natural medicine | herbal medicine name | weight(g) and compositional ratio (%) |
| --- | --- | --- |
| longan arillus | Longan Arillus(=Longanae Arillus) | 12 g (17.14 wt %) |
| Angelicae tenuissimae radix | Angelicae tenuissimae radix | 8 g (11.43 wt %) |
| Polygalae radix | Polygalae Radix | 8 g (11.43 wt %) |
| Puerariae Radix | Puerariae Radix | 12 g (17.14 wt %) |
| *Scutellaria* radix | Scutellariae Radix | 4 g (5.71 wt %) |
| Platycodi Radix | Platycodi Radix | 2 g (2.86 wt %) |
| Cimicifugae Rhizoma | Cimicifugae Rhizoma | 4 g (5.71 wt %) |
| Angelicae Dahuricae Radix | Angelicae Dahuricae Radix | 4 g (5.71 wt %) |
| Raphani Semen | Raphani Semen | 4 g (5.71 wt %) |
| Acorus Gramineri Rhizoma | Acori Gramineri Rhizoma | 12 g (17.14 wt %) |
| Total | | 70 g |

Example 2

Effect of Combined Extract of the Present Invention on Brain Cell Death Caused by MPTP The effects of longan arillus extract and combined extract (DG) and combined extract (MYH) prepared in <Example 1> on brain cell death caused by extracellularly treated MPTP <2-3-1> Concentration-Dependent Effect of Longan Arillus Extract on Brain Cell Death Induced by MPTP For MTT analysis, cultured SY—SY5Y cells were treated with longan arillus extract prepared in <Example 1-1> at concentrations of 3.125, 6.25, 12.5, 25 μg/ml, and after 2 hours, MPTP was added at the concentration of 400 μM, and then, cultured under 5% $CO_2$, at 37° C. At this time, control treated with medium alone and test group treated with MPTP alone were also prepared and used. After 48 hours, an MTT solution was added and cultured for 1 hour, and then, absorbance was measured using ELISA instrument.

As explained, cell viability of each group was obtained by measuring MTT reduction degree, and the results are shown in FIG. 1a.

As shown in FIG. 1a, cell viability of 400 μM MPTP-treated group was 62.75% compared to control, showing that cytotoxicity was induced. In contrast, against the cytotoxitity, cell viability of 3.125 μg/ml longan arillus extract-treated group increased to 123%, cell viability of 6.25 μg/ml longan arillus extract-treated group increased to 138%, and thereafter, cell protection activity continued.

From these results, it is confirmed that the longan arillus extract of the present invention may inhibit brain cell death caused by extracellularly-treated MPTP in a concentration-dependent manner.

<2-3-2> Concentration-Dependent Effects of Combined Extract (DG) on Brain Cell Death Caused by MPTP For MTT analysis, cultured SH-SY5Y cells were treated with combined extract (DG) prepared in <Example 1-2> at concentrations of 25, 50, 100, 200, 300 μg/ml, and after 2 hours, 400 μM of MPTP was added, and then, cultured under 5% $CO_2$ at 37° C. At this time, control treated with medium alone and test group treated with MPTP alone were also prepared and used. After 48 hours, an MTT solution was added and cultured for 1 hour, and then, absorbance was measured using ELISA instrument.

Figure 1B:
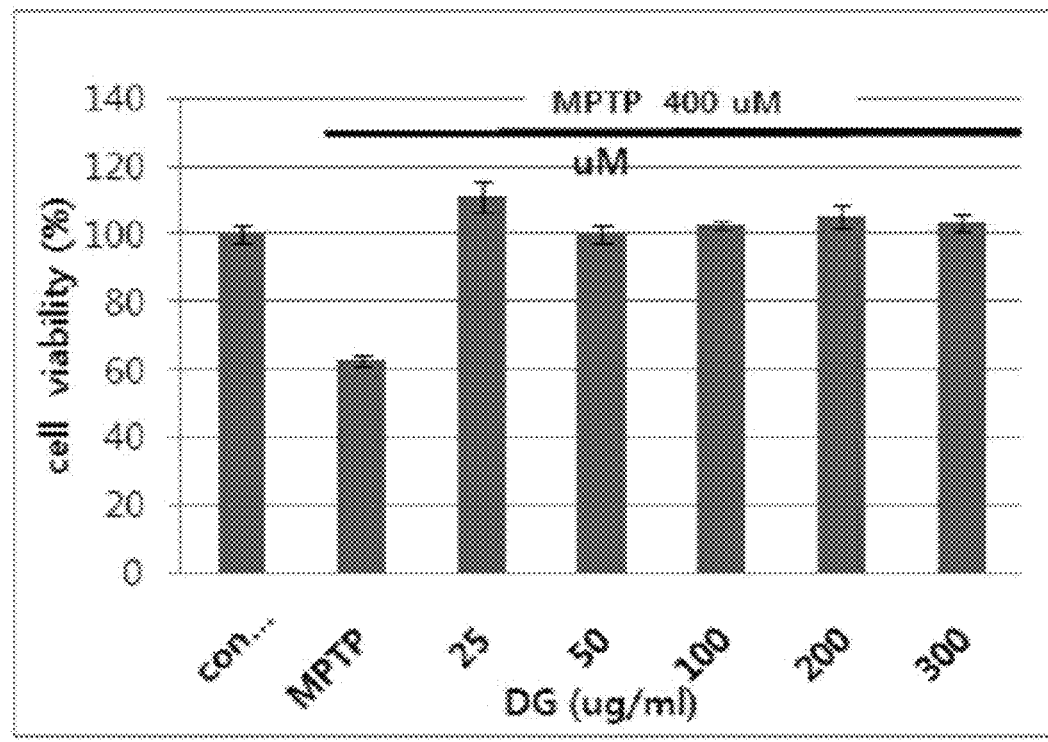
FIG. 1b shows the results of measurements of the effects of combined extract (DG) of longan arillus, Angelicae tenuissimae radix and Polygalae radix on brain cell death caused by MPTP with increasing concentration.

Cell viability of each group was obtained by measuring MTT reduction degree, and the results are shown in FIG. 1b.

As shown in FIG. 1b, cell viability of 400 μM MPTP-treated group was 62.13% compared to control, showing that cytotoxicity was induced. In contrast, against the cytotoxicity, cell viability of 25 μg/ml combined extract (DG)-treated group increased to 110%, and thereafter, cell protection activity continued in a concentration-dependent manner.

From these results, it is confirmed that the combined extract (DG) of the present invention may inhibit brain cell death caused by MPTP in a concentration-dependent manner.

<2-3-3> Comparison of Effects of Combined Extracts on Brain Cell Death Caused by MPTP with Varying Mixing Ratios For MTT analysis, cultured SH-SY5Y cells were treated with each combined extract prepared in <Example 1-2> at the concentrations of 25 μg/ml, and after 2 hours, 400 μM of MPTP was added, and then, cultured under 5% $CO_2$ at 37° C. At this time, control treated with medium alone and test group treated with MPTP alone were also prepared and used. After 48 hours, an MTT solution was added and cultured for 1 hour, and then, absorbance was measured using ELISA instrument.

Figure 1C:
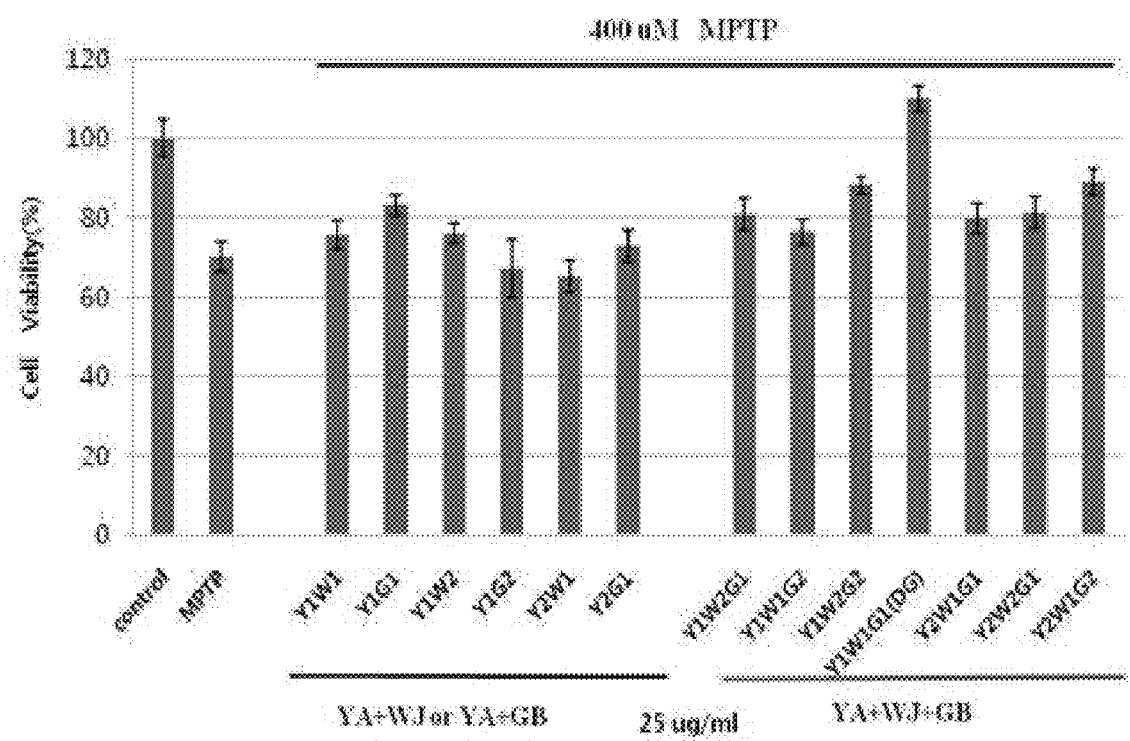
FIG. 1c shows the results of measurements of the effects of combined extract of longan arillus and Angelicae tenuissimae radix, or longan arillus and Polygalae radix, and combined extract of longan arillus, Angelicae tenuissimae radix and Polygalae radix on brain cell death caused by MPTP with increasing concentration. (YA or Y: longan arillus, WJ or W: Polygalae radix, GB or G: Angelicae tenuissimae radix, Y1W1: combined extract of longan arillus and Polygalae radix in the weight ratio of 1:1).

Cell viability of each group was obtained by measuring MTT reduction degree, and the results are shown in FIG. 1c.

As shown in FIG. 1c, cell viability of 400 μM MPTP-treated group was 70.21% compared to control, showing that cytotoxicity was induced. In contrast, against the cytotoxicity, cell viabilities of groups treated with combined extract consisting of two medicines were 65 to 75% thus showing cell protection activities. Particularly, combined extract of longan arillus and Polygalae radix has very effective cell protection activity when mixed at the weight ratio of 1:1~2, more preferably 1:1. And, combined extract of longan arillus and Angelicae tenuissimae radix has very effective cell protection activity when mixed at the weight ratio of 1:0.5~1, more preferably 1:1.

Meanwhile, cell viabilities of the groups treated with combined extracts of three medicines of longan arillus, Polygalae radix and Angelicae tenuissimae radix were 80 to 110%, thus showing increased cell protection activities. Particularly, it can be see that when longan arillus, Angelicae tenuissimae radix and Polygalae radix are mixed at the weight ratio of 1:0.5~2:0.5~2, more preferably at the weight ratio of 1:1:1, cell protection activities are more pronounced.

<2-3-4> Concentration-Dependent Effects of a Composition Comprising Combined Extract (MYH) of Longan Arillus, Angelicae Tenuissimae Radix and Polygalae Radix on Brain Cell Death Caused by MPTP For MTT analysis, cultured SH-SY5Y cells were treated with a composition comprising the combined extract of longan arillus, Angelicae tenuissimae radix and Polygalae radix prepared in <Example 1-3> at concentrations of 6.25, 12.5, 25, 50 μg/ml, and after 2 hours, 400 μM of MPTP was added, and then, cultured under 5% $CO_2$ at 37° C. At this time, control treated with medium alone and test group treated with MPTP alone were also prepared and used for test. After 48 hours, an MTT solution was added and cultured for 1 hour, and then, absorbance was measured using ELISA instrument.

Figure 1D:
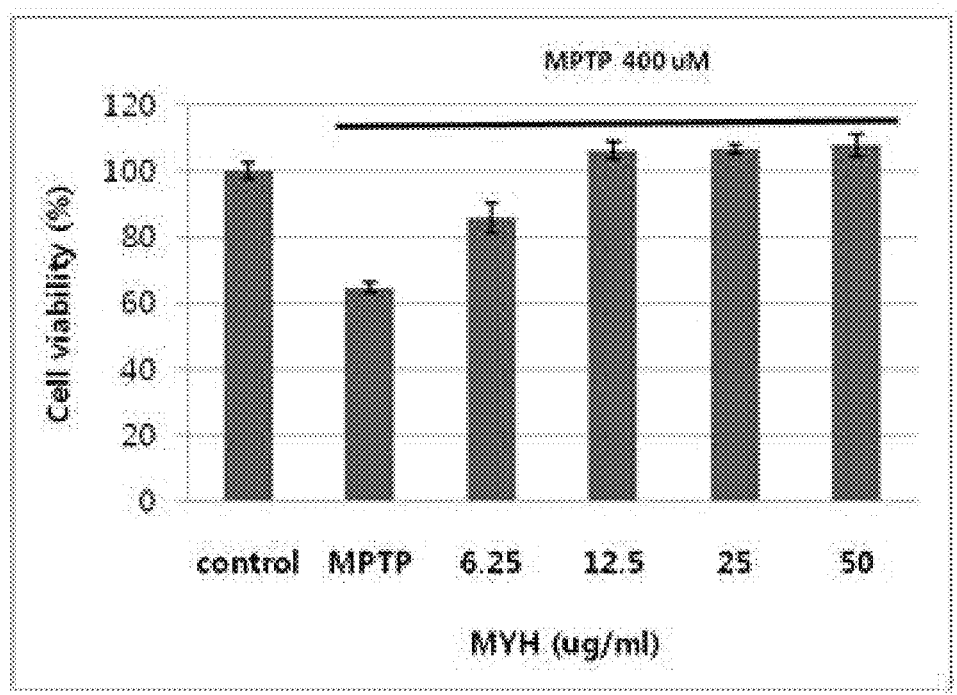
FIG. 1d shows the effects of combined extract (MYH) on brain cell death caused by MPTP with increasing concentration.

Cell viability of each group was obtained by measuring MTT reduction degree, and the results are shown in FIG. 1d.

As shown in FIG. 1d, cell viability of 400 μM MPTP-treated group was 64.74%, showing that cytotoxicity was induced. In contrast, against the cytotoxicity, the groups treated with combined extract (MYH) showed 85.86% cell protection activity at 6.25 μg/ml, and at the concentrations of 12.5 μg/ml, 25 μg/ml and 50 μg/ml, all the groups showed complete cell protection activities compared to control treated with medium alone.

From these results, it is confirmed that a composition (MYH) comprising combined extract of longan arillus, Angelicae tenuissimae radix and Polygalae radix may inhibit brain cell death caused by MPTP in a concentration-dependent manner.

Example 3

Effect of Longan Arillus Extract or Combined Extract for Inducing Autophagy in Brain Neurons To confirm expression of LC3 2 protein, a marker for showing autophagy inducing activity in PC12 cell line differentiated into neurons by NGF (nerve growth factor), western-blot test was conducted as follow.

<3-1> Medium Comprising Extract

The combined extract (I) or combined extract (II) of <Example 1> was diluted in DMEM medium (HyClone Laboratories, Hyclone Rd., Logan Utah, U.S.A.) containing 10% Fetal bovine serum and 1% antibiotics at various concentrations.

<3-2> Cell Culture

As neuron model, PC12 cell (differentiated by NGF, RCB0009, RIKEN BRC Cell Bank, Tsukuba, Ibaraki, Japan) originated from white mouse pheochromocytoma was selected.

The cells were cultured in DMEM medium containing 10% fetal bovine serum and 1% antibiotics, and were differentiated into neurons by NGF (nerve growth factor) prior to use for test.

<3-3> Identification of Autophagy-Inducing Activity

To confirm the effects of longan arillus extract or combined extract prepared in <Example 1> for inducing autophagy, the conversion rate of autophagy expression marker LC3 1 to LC3 2 was measured by western-blotting assay.

<3-3-1> Concentration-Dependent Autophagy-Inducing Activities of Longan Arillus Extract Cultured PC12 cells were treated with longan arillus extract prepared in <Example 1-1> respectively at the concentrations of 25 μg/ml, 50 μg/ml, 100 μg/ml, and cultured under 5% CO2 at 37° C. for 24 hours, and then, collected and centrifuged at 2500 rpm for 5 minutes and washed with FBS (pH 7.2) twice. The obtained cells were reacted with mitochondrial lysis buffer (50 mM Tris pH 7.4, 150 mM NaCl, 2 mM EDTA, 2 mM EGTA, 0.2% Triton X-100, 0.3% NP-40, 100 μM PMSF, 10 μg/ml leupeptin, 2 μg/ml aprotinin) at 4° C. for 20 minutes to separate proteins, and then, centrifuged at 13,200 rpm for 20 minutes. In the obtained supernatant, proteins were quantified according to Bradford's method (Bio-Rad Laboratories, Hercules, Calif., USA).

The equal amount of cell lysate was mixed with SDS loading buffer and heated at 99° C. for minutes, and then, subjected to 15% SDS-polyacrylamide gel electrophoresis (PAGE). To separate proteins based on the molecular weight, single 15% SDS-polyacrylamide gel was used. Proteins electrophoresed at 150V per gel were charged at room temperature for 1 hour by semi-dry method to move them onto a nitrocellulose membrane. The nitrocellulose membrane was reacted with blocking buffer (5% skim milk in Tris-buffered saline containing 0.1% Tween-20) at room temperature for 30 minutes to prevent non-specific antibody bonding. LC3, antibody to GapDH (Cell Signaling Technology Inc. purchased from <Beverly, Mass., U.S.A.>) was diluted with 5% skim milk containing 0.1% Tween-20/Tris-buffered saline at a ratio of 1:1000 and reacted at 4° C. overnight, and then, secondary antibody (anti-rabbit IgG conjugated horse-radish peroxidase, Cell Signaling Technology Inc. purchased from <Beverly, Mass., U.S.A.>) was diluted at a ratio of 1:2000 and reacted for 1 hour. The nitrocellulose membrane was washed with TBS three times, and then, developed an ECL film using ECL kit. At this time, control treated with medium alone was also prepared and used for experiment, and GapDH proteins were measured to confirm the equal amount. Conversion rate of LC3 1 to LC3 2 was confirmed and the experiment results are shown in FIG. 2a.

Figure 2A:
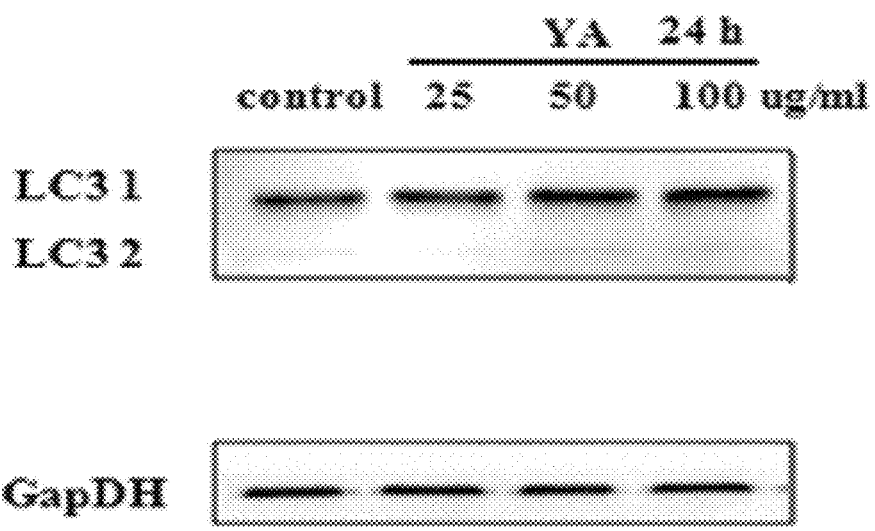
FIG. 2a shows the experiment results of autophagy-inducing activities of longan arillus extract (YA) with increasing concentration.

As shown in FIG. 2a, in the group treated with 100 μg/ml longan arillus extract, the ratio of LC3 2/LC3 1 increases compared to control, and thus it can be seen that longan arillus extract induces expression of LC3 2 proteins.

<3-3-2> Comparison of Autophagy Inducing Activities of Longan Arillus Extract and Combined Extract (DG)

Cultured PC12 cells were treated respectively with longan arillus prepared in <Example 1-1> at the concentration of 100 μg/ml and combined extract (DG) prepared in <Example 1-2> at the concentration of 300 μg/ml, and cultured under 5% CO$_2$ at 37° C. for 24 hours, and then, subjected to experiment by the same method as described in <Example 3-3-1>. At this time, control treated with medium alone was prepared and used for experiment, and GapDH proteins were measured to confirm the equal amount. The conversion rate of LC3 1 to LC3 2 was confirmed and the experiment results are shown FIG. 2b.

Figure 2B:
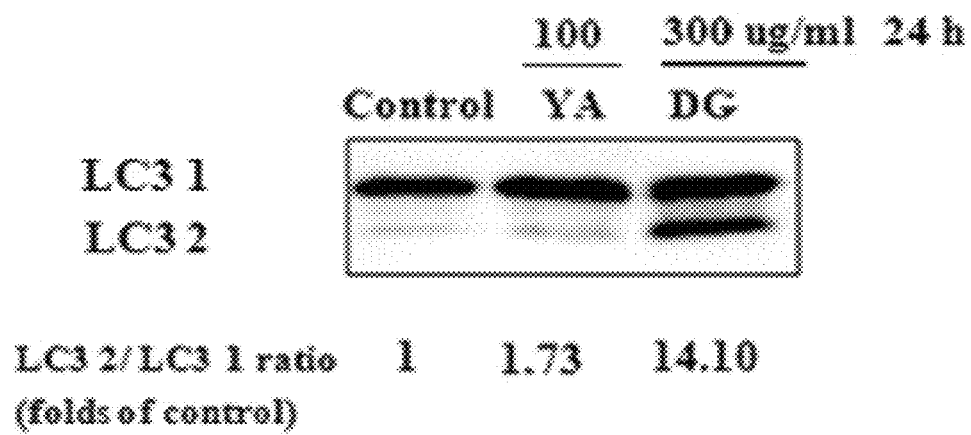
FIG. 2b shows the experiment results comparing autophagy-inducing activities of longan arillus extract (YA) and combined extract (DG).
Figure 2B:

As shown in FIG. 2b, in the group treated with 100 μg/ml longan arillus extract, the conversion rate of LC3 1 to LC3 2 increased to 1.73, while in the group treated with 300 μg/ml combined extract DG, very distinct LC3 2 protein expression was indicated, and the conversion rate of LC3 1 to LC3 2 was identified to be 14.10.

From these results, it can be seen that combined extract of longan arillus, Angelicae tenuissimae radix and Polygalae radix as well as longan arillus extract have very excellent autophagy-inducing effects.

<3-3-3> Concentration-Dependent Autophagy-Inducing Activity of Combined Extract (DG)

Cultured PC12 cells were treated with combined extract (DG) prepared in <Example 1-2> at various concentrations of 75, 150, 300, 600 μg/ml, and cultured under 5% CO$_2$ at 37° C. for 24 hours, and then, subjected to experiment by the same method as described in <Example 3-3-1>. At this time, control treated with medium alone was also prepared and used for experiment, and GapDH proteins were measured for confirming the equal amount. The conversion rate of LC 3 1 to LC3 2 was confirmed and the experiment results are shown in FIG. 2c.

Figure 2C:
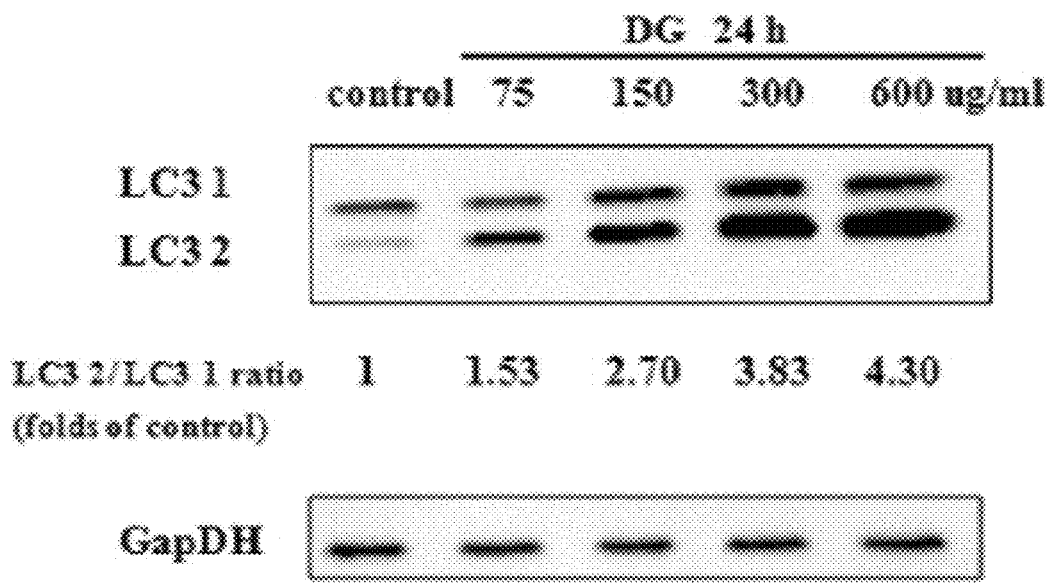
FIG. 2c shows the experiment results of autophagy-inducing activities of combined extract (DG) with increasing concentration.

As shown in FIG. 2c, it is confirmed that the combined extract (DG) of the present invention exhibits increased expression of LC3 2 protein, which is a marker indicating autophagy inducing effect, or increased conversion rate of LC3 1 to LC3 2 with increasing concentration, and that the combined extract of the present invention has increased autophagy-inducing effect with increasing concentration.

<3-3-4> Autophagy Inducing Activity of Combined Extract (DG) with Time Lapse

Cultured PC12 cells were treated with combined extract (DG) prepared in <Example 1-2> at the concentrations of 300 μg/ml, and cultured under 5% CO$_2$ at 37° C. for various times (6, 12, 24, 48 hours), and then, subjected to experiment as described in <Example 3-3-1>. At this time, control treated with medium alone was also prepared and used for experiment, and GapDH proteins were measured for confirming the equal amount. The conversion rate of LC 3 1 to LC 3 2 was confirmed and the experiment results are shown in FIG. 2d.

Figure 2D:
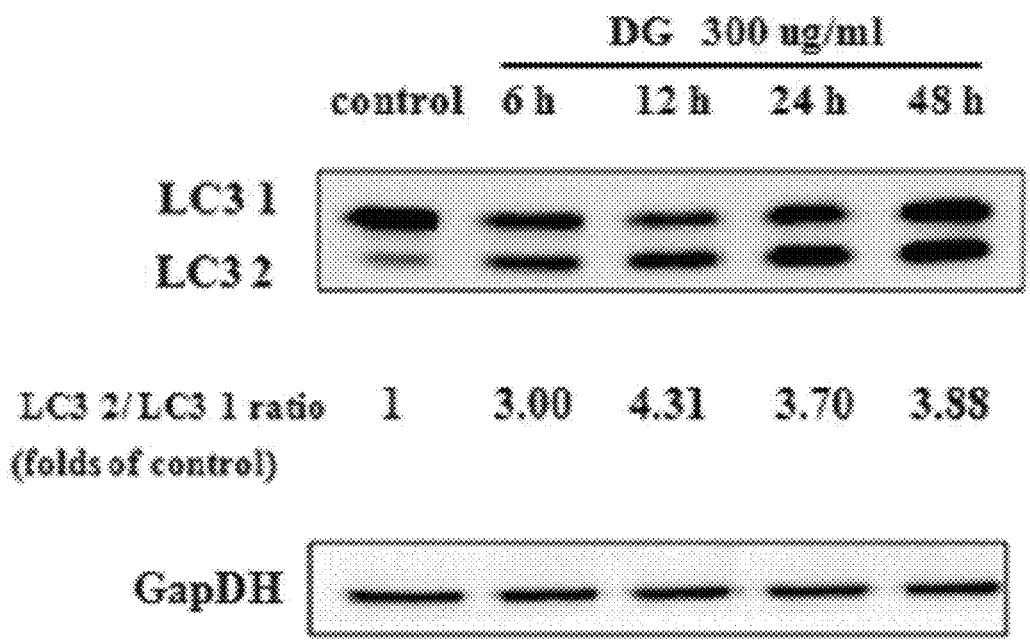
FIG. 2d shows the experiment results of autophagy-inducing activities of combined extract (DG) with time lapse.

As shown in FIG. 2d, the combined extract (DG) of the present invention exhibited increased expression of LC3 2 protein, which is a marker indicating autophagy inducing effect, or increased conversion rate of LC3 1 to LC3 2 with time lapse, and particularly after 12 hours, conversion rate of LC3 2/LC3 1 increased the most.

<3-3-5> Verification of Autophagy Inducing Effect of Combined Extract (DG) Using Autophagy Inhibitor To verify the autophagy-inducing effect of the combined extract (DG) of the present invention, an experiment using autophagy inhibitor was conducted. 3-Methyladenine (3MA) used in this experiment is a specific autophagy inhibitor, and is commonly used in an experiment for verifying autophagy-inducing effect of drugs since it inhibits autophagy effect caused by drug (Seglen P. O, Gordon P. B. (1982). 3-Methyladenine: specific inhibitor of autophagic/lysosomal protein degradation in isolated rat hepatocytes. Proceedings of the National Academy of Sciences of United States of America, 79; 1889-1892, 1982.).

Cultured PC12 cells were respectively treated with 300 μg/ml combined extract (DG), and with 300 μg/ml of combined extract (DG) and 10 mM of 3MA, and cultured under 5% CO$_2$ at 37° C. for 24 hours, and then, subjected to experiment as described in <Example 3-3-1>. At this time, control treated with medium alone was also prepared and used for experiment, and GapDH proteins were measured for confirming the equal amount. The conversion rate of LC 3 1 to LC 3 2 was confirmed and the experiment results are shown in FIG. 2e.

Figure 2E:
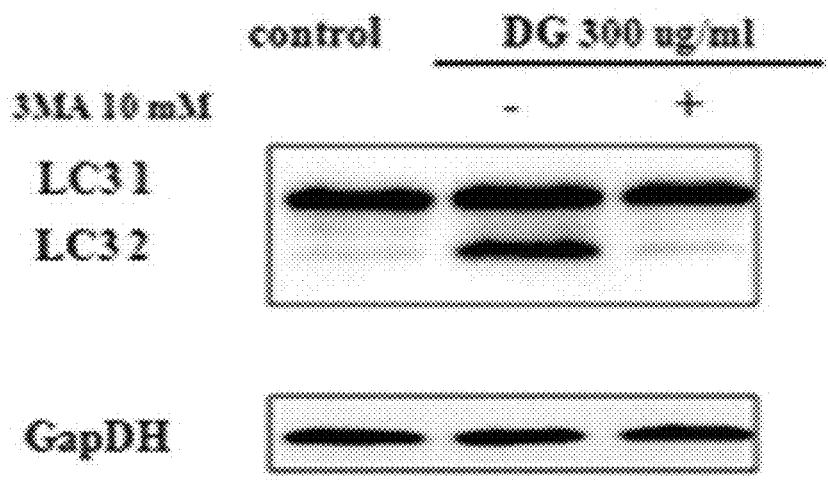
FIG. 2e shows the experiment results verifying autophagy-inducing effects of combined extract (DG) using autophagy inhibitor.

As shown in FIG. 2e, the expression level of LC3 2 proteins observed in the test group treated with combined extract (DG) alone decreased to the level of control in the test group treated with combined extract (DG) and 3MA, thus verifying that the combined extract (DG) of the present invention inherently has autophagy-inducing effect.

<3-3-6> Concentration-Dependent Autophagy-Inducing Activity of Combined Extract (MYH)

Cultured PC12 cells were treated with combined extract (MYH) prepared in <Example 1-3> at various concentrations (100, 400, 800, 1200 μg/ml) and cultured under 5% $CO_2$ at 37° C. for 24 hours, and then, subjected to experiment as described in <Example 3-3-1>. At this time, control treated with medium alone was also prepared and used for experiment, and GapDH proteins were measured for confirming the equal amount. The conversion rate of LC3 1 to LC3 2 was confirmed and the experiment results are shown in FIG. 2f.

Figure 2F:
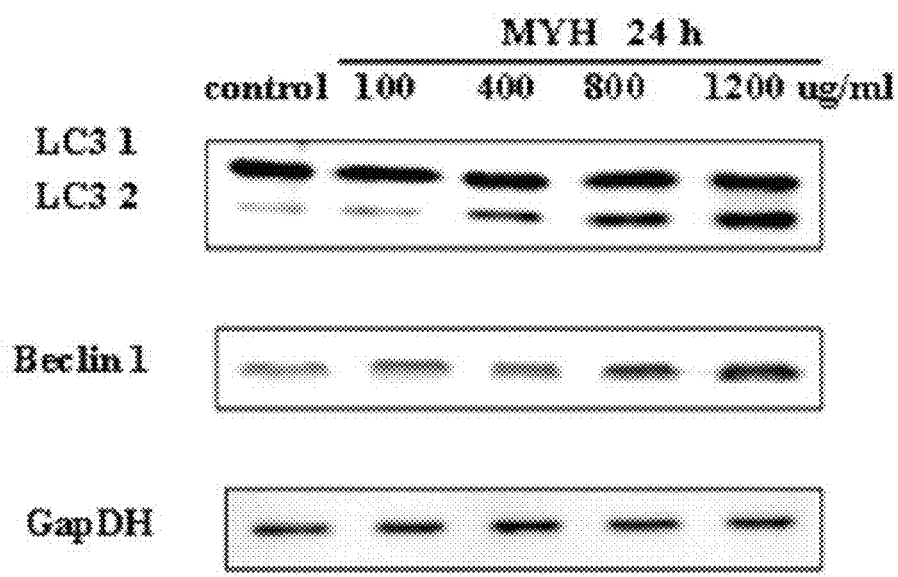
FIG. 2f shows the experiment results of autophagy-inducing activities of combined extract (MYH) with increasing concentration.

As shown in FIG. 2f, it is confirmed that the combined extract (MYH) of the present invention exhibits increased expression of LC3 2 protein, which is a marker indicating autophagy inducing effect, or increased conversion rate of LC3 1 to LC3 2 with increasing concentration, and that the combined extract (MYH) of the present invention has increased autophagy-inducing effect with increasing concentration.

<3-3-7> Autophagy Inducing Activity of Combined Extract (MYH) with Time Lapse

Cultured PC12 cells were treated with combined extract (MYH) prepared in <Example 1-3> at the concentration of 400 μg/ml and cultured under 5% $CO_2$ at 37° C. for various times (6, 12, 24 hours), and then, subjected to experiment as described in <Example 3-3-1>. At this time, control treated with medium alone was also prepared and used for experiment, and GapDH proteins were measured for confirming the equal amount. The conversion rate of LC3 1 to LC3 2 was confirmed and the experiment results are shown in FIG. 2g.

Figure 2G:
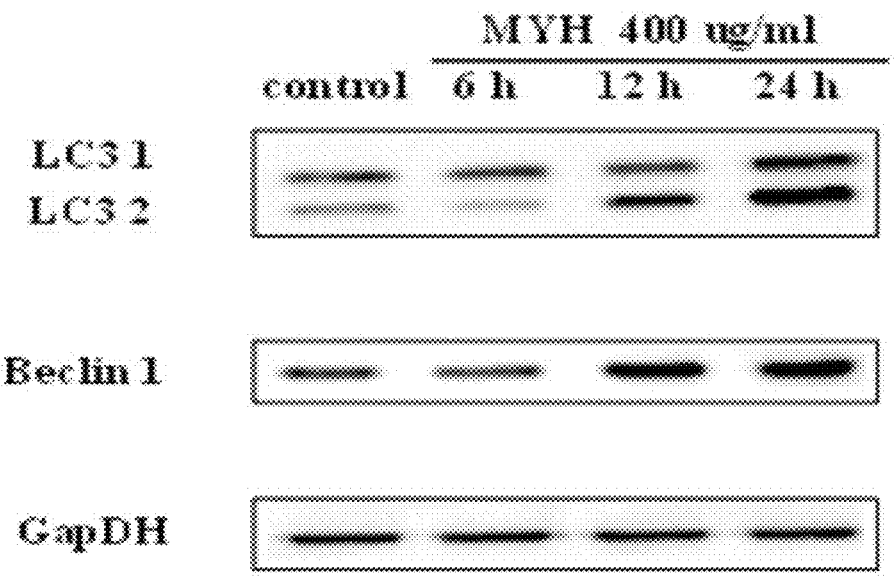
FIG. 2g shows the experiment results of autophagy-inducing activities of combined extract (MYH) with time lapse.

As shown in FIG. 2g, it is confirmed that the combined extract (MYH) of the present invention exhibits increased expression of LC3 2 protein, which is a marker indicating autophagy inducing effect, or increased conversion rate of LC3 1 to LC3 2 with time lapse, compared to control.

<3-3-8> Verification of Autophagy Inducing Effect of Combined Extract (MYH) Using Autophagy Inhibitor To clearly verify the autophagy-inducing effect of the combined extract (MYH) of the present invention, an experiment using autophagy inhibitor was conducted. Cultured PC12 cells were respectively treated with 400 fig/ml combined extract (MYH), and with 400 μg/ml combined extract (MYH) and 3MA 10 mM, and cultured under 5% $CO_2$ at 37° C. for 24 hours, and then, subjected to experiment as described in <Example 3-3-1>. At this time, control treated with medium alone was also prepared and used for experiment, and GapDH proteins were measured for confirming the equal amount. The conversion rate of LC3 1 to LC3 2 was confirmed and the experiment results are shown in FIG. 2h.

Figure 2H:
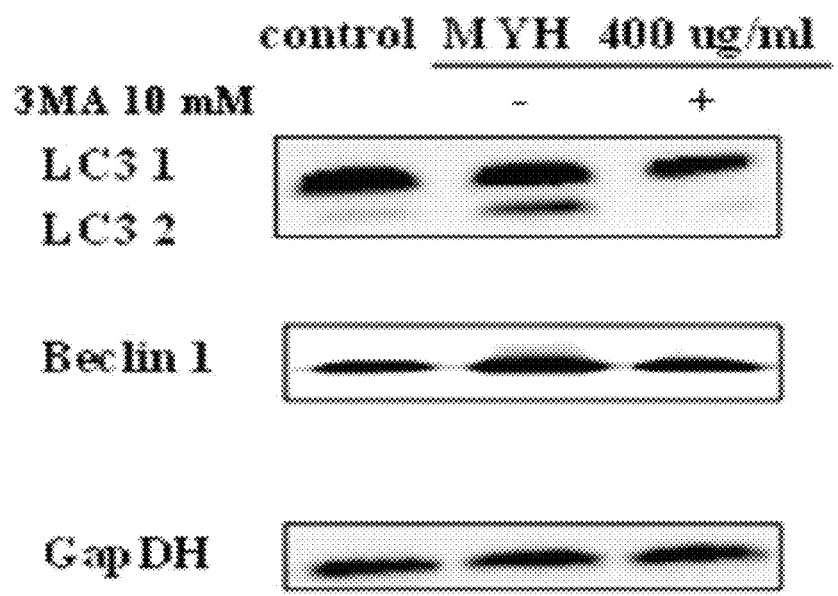
FIG. 2h shows the experiment results verifying autophagy-inducing effects of combined extract (MYH) using autophagy inhibitor.

As shown in FIG. 2h, the expression level of LC3 2 protein observed in the test group treated with combined extract (MYH) alone decrease to the level of control in the test group treated with combined extract (MYH) and 3MA, thus verifying that the combined extract (MYH) of the present invention inherently has autophagy-inducing effect.

Example 4

Effects of the Combined Extract of the Present Invention on Behavior Disorder and Brain Cell Death in Parkinson's Disease Animal Model Caused by MPTP Administration <4-1> Combined Extract Used in the Experiment The combined extract (DG) of <Example 1-2> and the combined extract (MYH) of <Example 1-3> were diluted in physiological saline in various concentrations and subsequently used in the experiment.

<4-2> Treatment of Experiment Animal

<4-2-1> Treatment of Experiment Animal with Combined Extract (DG)

Mice were divided into 4 groups with 9 mice per each group. Group 1 (control) and Group 2 (MPTP group) received oral administrations of 5 ml of a physiological saline solution per kg of mouse body weight, and Group 3 (combined extract 50 mg/kg administration group) and group 4 (combined extract 100 mg/kg administration group) received oral administration of each combined extract dissolved in physiological saline once a day for 6 consecutive days. On Day 3, 2 hours after final administration, Group 1 (control) received intraperitoneal administration of a physiological saline solution at 5 ml per kg of mouse body weight 4 times a day (Acute) at the interval of 2 hours, and Group 2, Group 3 and Group 4 received intraperitoneal administration of MPTP dissolved in physiological saline at the concentration of 20 mg/kg of body weight 4 times a day (Acute) at the interval of 2 hours.

<4-2-2> Treatment of Experiment Animal with Combined Extract (MYH)

Mice were divided into 3 groups with 7 mice per each group. Group 3 (MYG 100 mg/kg administration group) received oral administration of combined extract (MYH) dissolved in a physiological saline solution once a day for 3 days, Group 1 (control) and Group 2 (MPTP group) received oral administration of the equal amount of a physiological saline solution. 3 days after drug administration, Group 2 and Group 3 received intraperitoneal administration of MPTP dissolved in physiological saline solution at the concentration of 20 mg/kg of body weight 4 times a day (acute) at the interval of 2 hours. 7 days after MPTP administration, mouse was anesthetized to be killed, and then, the brain tissue was fixed with 4% paraformaldehyde (PFA) and stored at −80° C.

<4-3> Effect of Combined Extract (DG) for Improving Behavior Disorder

<4-3-1> Behavior Test; Pole Test

On the next day after completing the MPTP administration, a pole test was conducted on a pole with height of 50 cm and diameter of 1 cm. On the pole, C57BL/6 mouse was laid with its head pointing upward, and the time for turning 180° around the top and for descending while turning until four legs reach the ground was measured. Each mouse was practiced 3 times, and then, the experiment was conducted 7 times, and the results are shown in FIG. 3a or FIG. 3b.

Figure 3A:
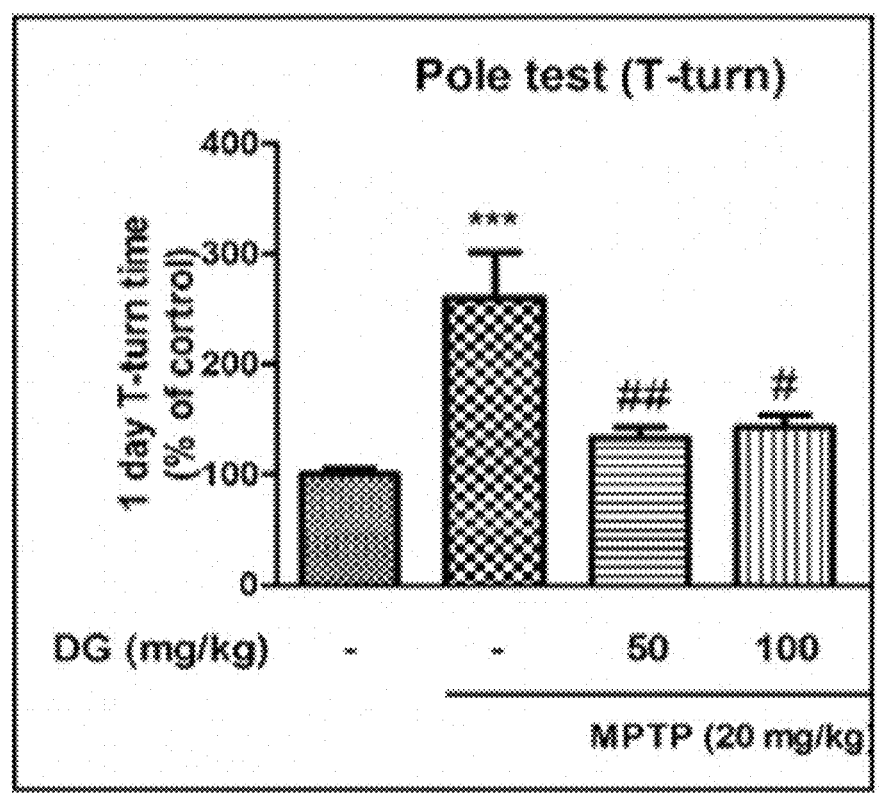
FIG. 3a is a graph showing pole test T-turn results (%) of combined extract (DG) in a C57BL/6 mouse with Parkinson's disease induced by MPTP administration. (each numerical value indicates mean±standard deviation, and ** indicates $p<0.01$, # indicates $p<0.05$, ## indicates $p<0.01$ compared to control)
Figure 3B:
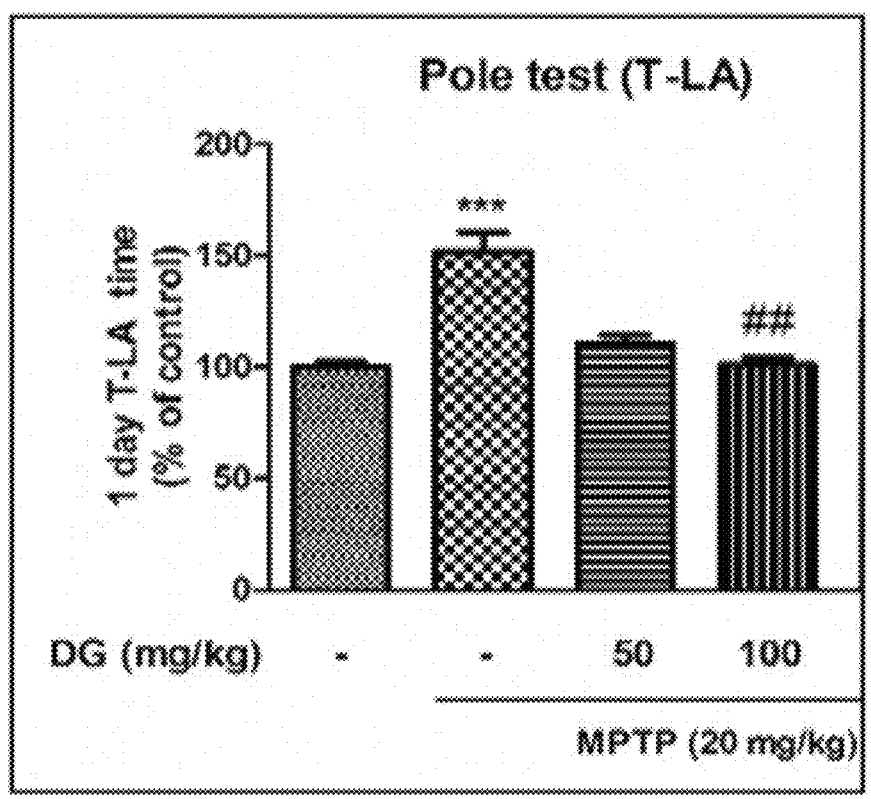
FIG. 3b is a graph showing pole test T-LA results (%) of combined extract (DG) in a C57BL/6 mouse with Parkinson's disease induced by MPTP administration. (each numerical value indicates mean±standard deviation, and ** indicates $p<0.01$, # indicates $p<0.05$, ## indicates $p<0.01$ compared to control)

As shown in FIG. 3a or FIG. 3b, MPTP group, when compared to control, showed T-turn and T-LA times of 260.21% and 151.82%, respectively, indicating that behavior disorder was induced by MPTP, while Group 3 (50 mg/kg combined extract administration group) showed T-turn and T-LA times of 133.10% and 110.51%, and Group 4 (100 mg/kg combined extract administration group) showed T-turn and T-LA times of 143.05% and 121.85%. These results confirmed that both T-turn and T-LA decreased in a concentration-dependent manner.

<4-3-2> Behavior Test; Rota-Rod Test 1 day after completing administration of the combined extract of the present invention (5 days after MPTP administration), a mouse was put on a plastic rod (diameter of 1 inch) of Rotarod B1001, B.S Technolab INC., Korea, set up at 8 rpm in an accelerator mode, and trained for 5 minutes. After 24 hours, the Rotarod was set up at 16 rpm in an accelerator mode and the experiment was conducted, and the results are shown in FIG. 3c.

Figure 3C:
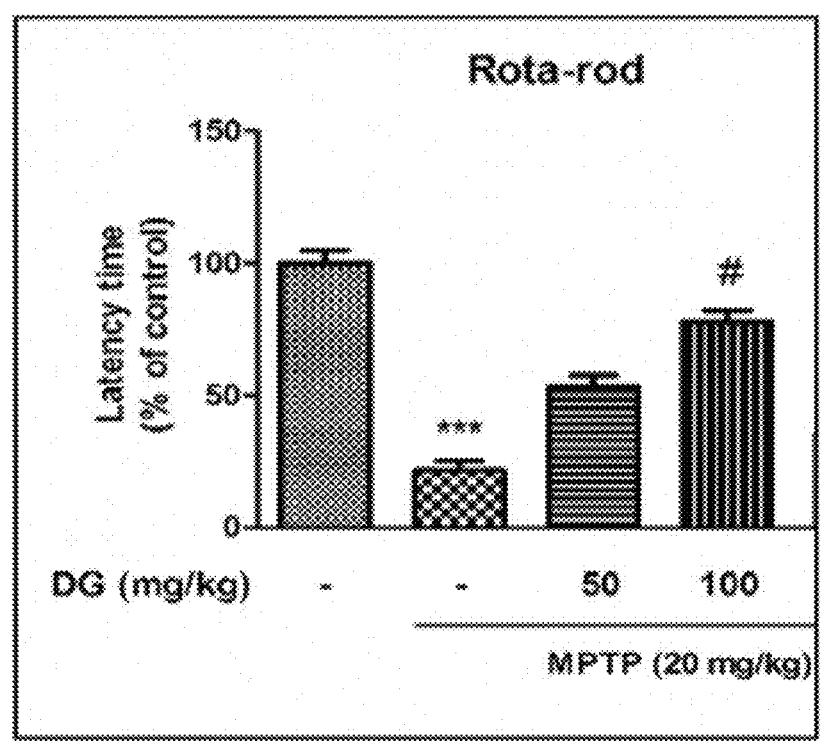
FIG. 3c is a graph showing Rota-rod test results (%) of combined extract (DG) in a C57BL/6 mouse with Parkinson's disease induced by MPTP administration. (each numerical value indicates mean±standard deviation, and *** indicates $p<0.001$ compared to control, and # indicates $p<0.05$ compared to group treated with MPTP alone)

As shown in FIG. 3c, MPTP group showed decreased latency time of 21.69%, as analyzed by % of control, indicating that behavior disorder was induced by MPTP, while Group 3 (50 mg/kg combined extract administration group)

showed 53.24% and Group 4 (100 mg/kg combined extract administration group) showed 77.89%, thereby confirming that latency time significantly increased.

As results of the behavior test, it is confirmed that the combined extract (DG) of the present invention shows significant improvement effect against behavior disorder caused by MPTP.

<4-4> Evaluation of Dopaminergic Neuron Protection Activity of Combined Extract (DG)

After completing the pole-test and Rotarod-test (7 days after MPTP administration), mice of each group were killed, and then, brain tissues (substantia nigra and striatum) were removed. The brain tissues were dehydrated with hydrogen peroxide, and reacted with primary antibody of Tyrosine hydroxylase (TH, millipore, rabbit origin 1:2000, purchased from Chemicon International Inc. <Temecula, Calif., USA>) overnight, and then, subjected to ABC reaction (ABC kit, purchased from Vector Laboratories <Burlingame, Calif., USA>) using secondary antibody of biotinylated anti-rabbit (goat origin, purchased from Vector Laboratories <Burlingame, Calif., USA>), and colored with Diaminobenzidine. Dopaminergic neuron protection effect was analyzed by counting the number of TH positive cells in substantia nigra, and evaluated by measuring optical density in striatum, and the results are shown in FIG. 3d and FIG. 3e.

Figure 3D:
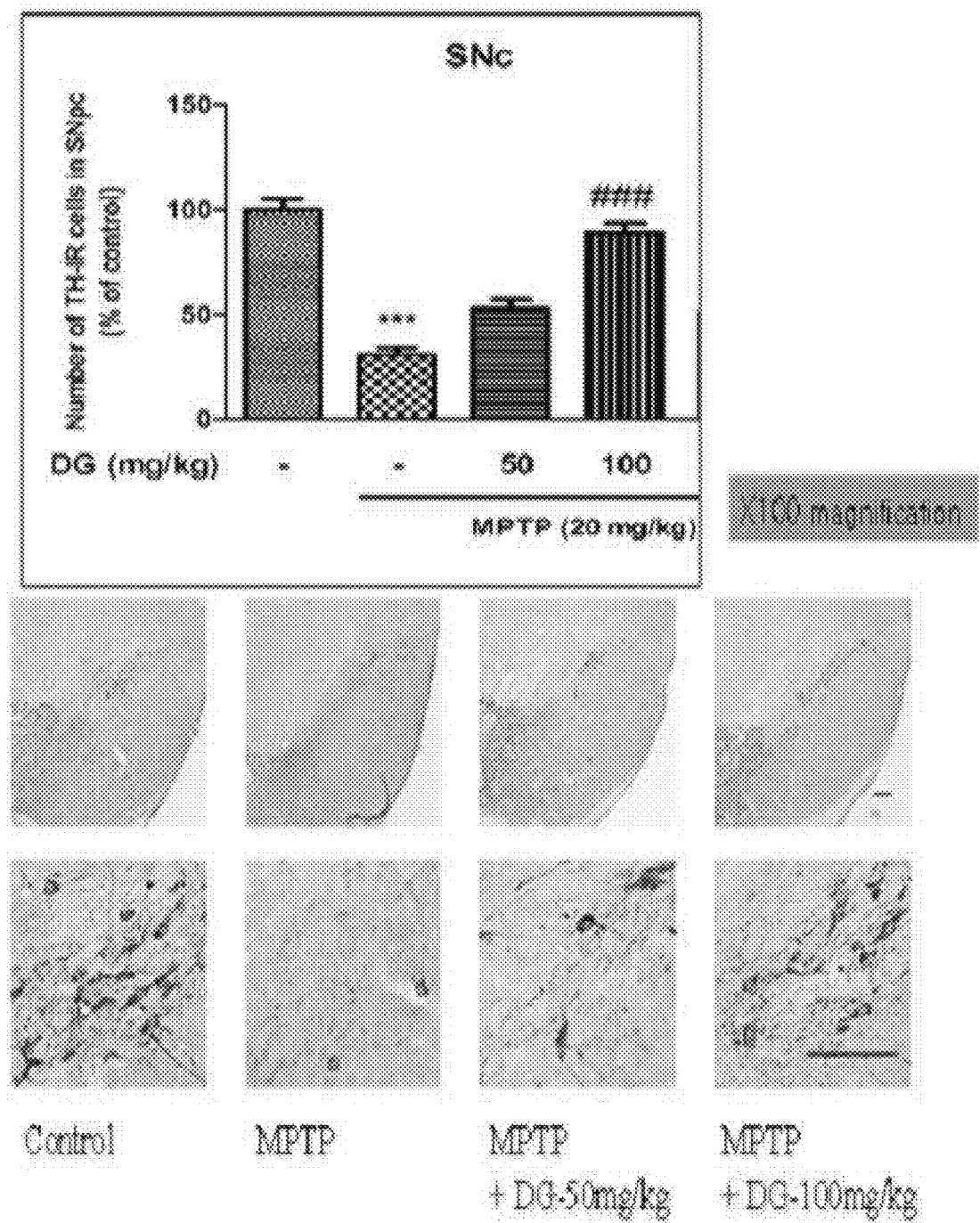
FIG. 3d is a graph showing the results of the measurements of inhibition activities of combined extract (DG) against decrease in tyrosine hydroxylase positive cells in substantia nigra in a C57BL/6 mouse with Parkinson's disease induced by MPTP administration, and a photograph showing the inhibition activity of DG(×100). (Scale bar is 100 μm, each numerical value indicates mean±standard deviation, and ### indicates $p<0.001$ compared to a group treated with MPTP alone)

As shown in FIG. 3d, MPTP group showed 30.82% of TH positive cell number in substantia nigra, as analyzed by % of control, indicating that cell damage was induced, while in 50 mg/kg combined extract-administered group, it increased to 52.75% and in 100 mg/kg combined extract-administered group, it increased to 89.19% thus showing protection effect against cytotoxicity induced by MPTP. In particular, in the 100 mg/kg administered group, TH positive cell number increased statistically significantly.

Figure 3E:
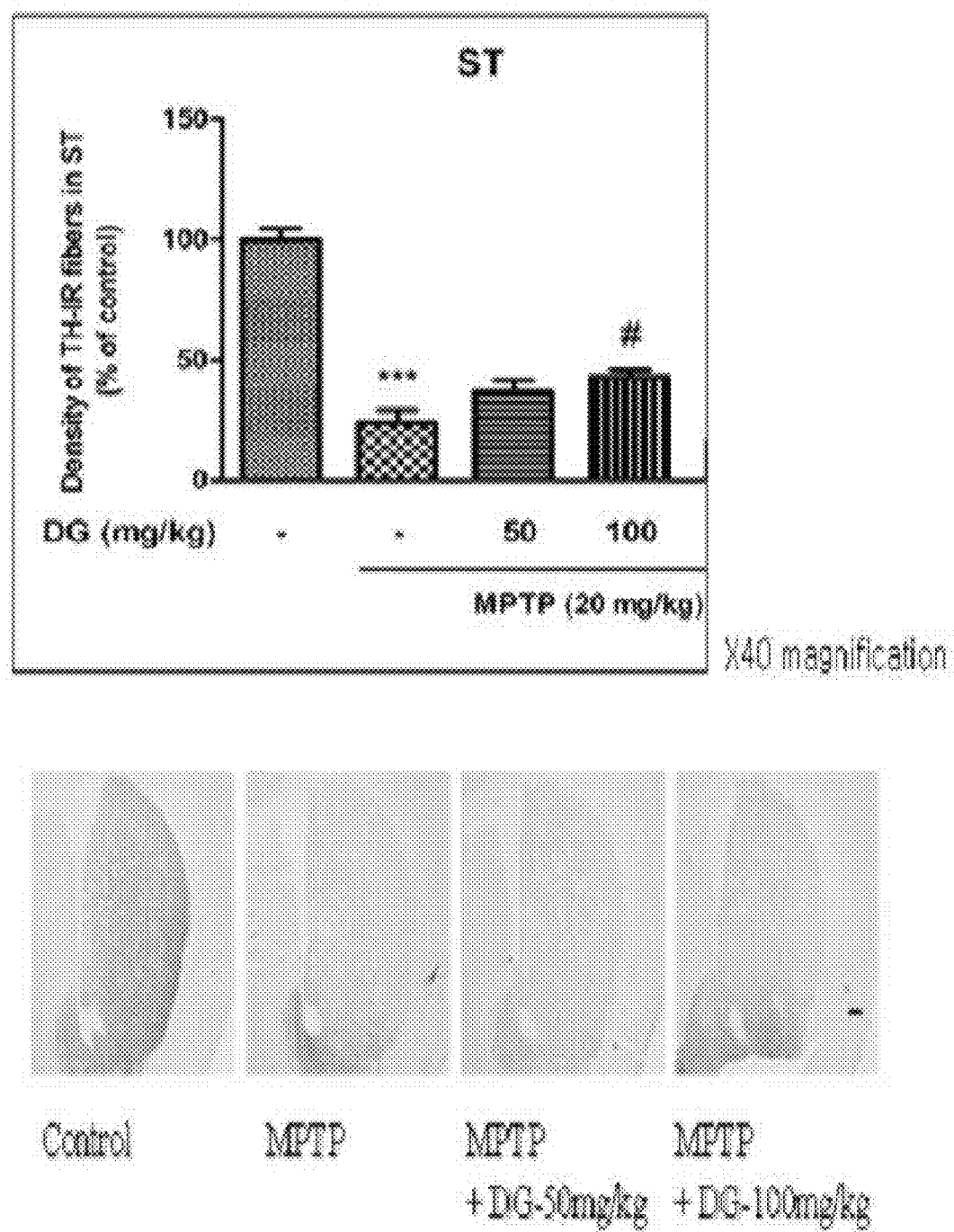
FIG. 3e is a graph showing the results of the measurements of inhibition activities of combined extract (DG) indicated by a decrease in optical density in striatum of a C57BL/6 mouse with Parkinson's disease induced by MPTP administration, and a photograph showing the inhibition activity of DG(×40) (Scale bar is 200 μm, each numerical value indicates mean±standard deviation, and *** indicates $p<0.001$ compared to control, and # indicates $p<0.05$ compared to group treated with MPTP alone)

Meanwhile, as shown in FIG. 3e, MPTP group showed 26.30% of optical density in striatum, as analyzed by % of control, indicating that dopaminergic neuron damage was induced, while in 50 mg/kg combined extract-administered group, it increased to 36.31% and in 100 mg/kg administered group, it increased to 43.42% thus confirming dopamine cell protection effect. In particular, in 100 mg/kg administered group, optical density increased statistically significantly.

These results confirmed that the combined extract (DG) of the present invention exhibits concentration-dependently excellent dopaminergic neuron protection activity in substantia nigra and striatum.

Figure 3F:
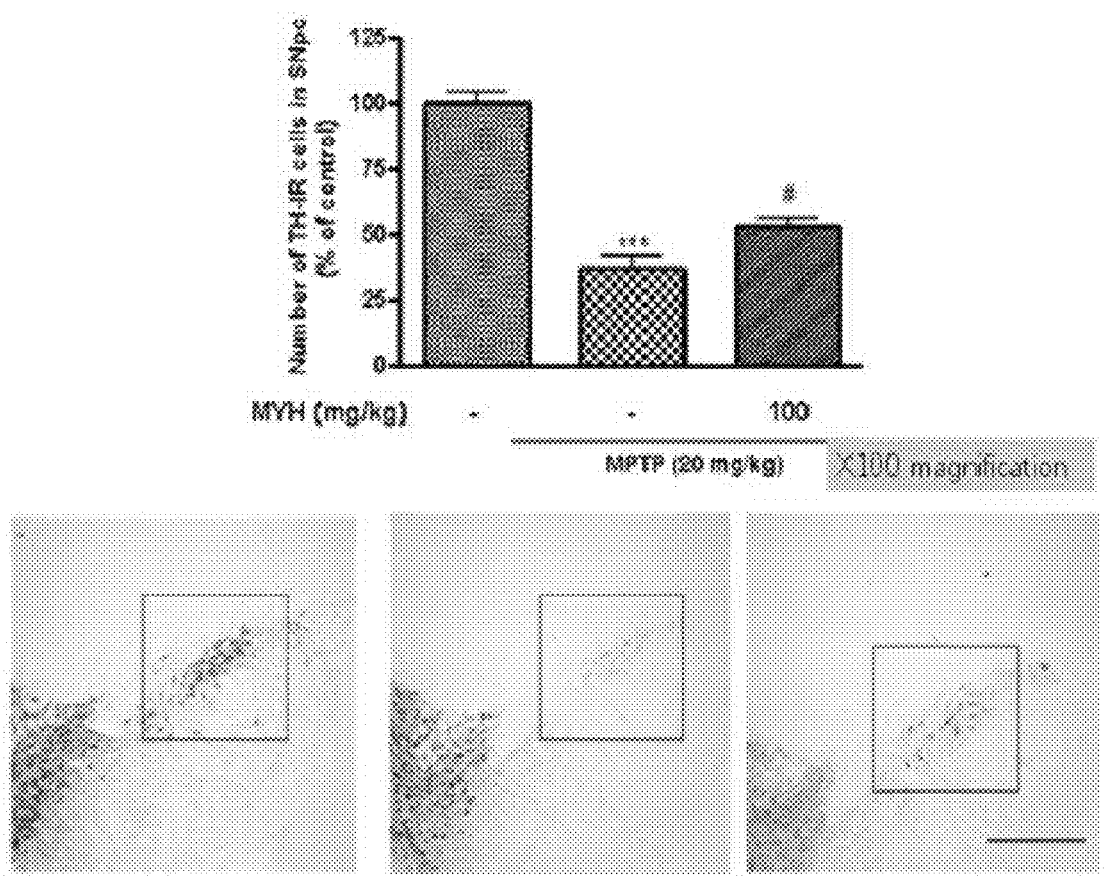
FIG. 3f is a graph showing the results of measurements of inhibition activities of combined extract (MYH) indicated by a decrease in tyrosine hydroxylase positive cells in substantia nigra of a C57BL/6 mouse with Parkinson's disease induced by MPTP administration, and a photograph showing the inhibition activity of MYH(×40). (Scale bar is 100 μm, each numerical value indicates mean±standard deviation, and *** indicates $p<0.001$ compared to control, and # indicates $p<0.001$ compared to a group treated with MPTP alone)
Figure 3G:
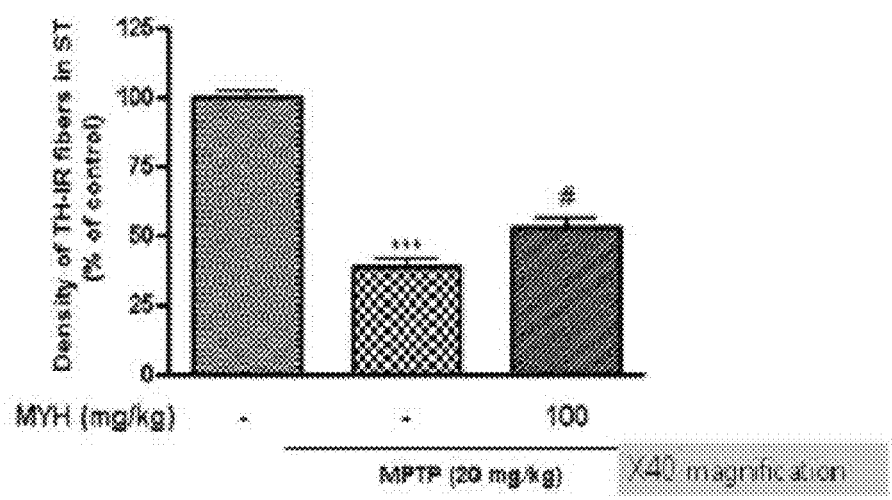
FIG. 3g is a graph showing the results of measurements of inhibition activities of combined extract (MYH) induced by a decrease in optical density in striatum of a C57BL/6 mouse with Parkinson's disease induced by MPTP administration, and a photograph showing the inhibition activity of MYH(×100) (Scale bar is 200 μm, each numerical value indicates mean±standard deviation, and *** indicates $p<0.001$ compared to control, and # indicates $p<0.05$ compared to group treated with MPTP alone)
Figure 3G:
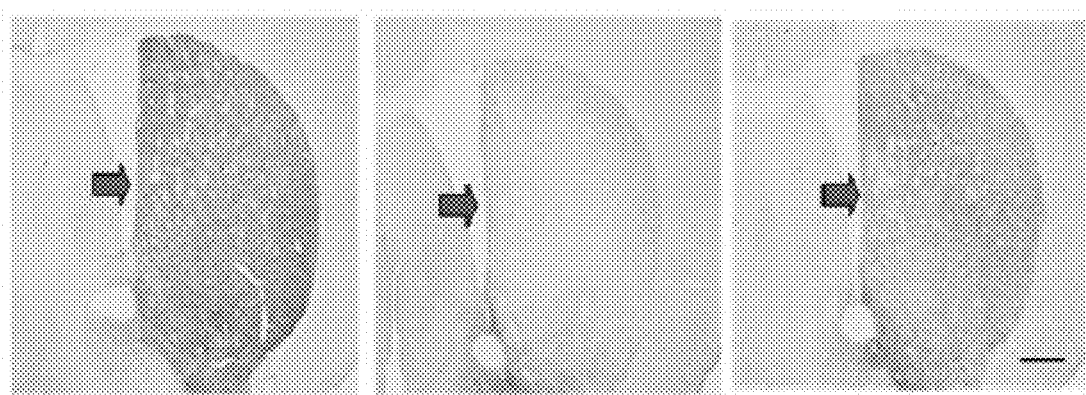

<4-5> Evaluation of Dopaminergic Neuron Protection Activity of Composition Comprising Combined Extract (MYH) of Longan Arillus, Angelicae Tenuissimae Radix and Polygalae Radix The brain tissues prepared in <Example 4-2-2> were treated by the method described in <Example 4-4>, and then, to evaluate dopaminergic neuron protection effect, the number of TH positive cells were counted and analyzed in substantia nigra, and optical density was measured in striatum, and the results are shown in FIG. 3f and FIG. 3g.

As shown in FIG. 3f, MPTP group showed 36.7% of TH positive cell number in substantia nigra, as analyzed by % of control, indicating that cell damage was induced by MPTP, while in 100 mg/kg MYH-administered group, it increased to 53.04% thus confirming protection effect against MPTP-induced cytotoxicity.

Meanwhile, as shown in FIG. 3g, MPTP group showed 37.79% of optical density in striatum, as analyzed by % of control, indicating that dopamine cell damage was induced by MPTP, while in 100 mg/kg MYH-administered group, it increased to 53.10%, thus confirming dopaminergic neuron protection effect.

These results confirmed that the composition (MYH) comprising combined extract of longan arillus, Angelicae tenuissimae radix and Polygalae radix exhibits concentration-dependently excellent dopaminergic neuron protection activity in substantia nigra and striatum.

Experimental Example 1

Effect of the Combined Extract of the Present Invention on Brain Cell Death

<1-1> Effect of Combined Extract (DG) on Brain Cell Death

To measure the effect of the combined extract (DG) of the present invention on cell viability, cytotoxycity measurement method (MTT Cell Proliferation assay) well known in the field was used.

For MTT analysis, cultured SH-SY5Y cells were treated with the combined extract (DG) prepared in <Example 1-2> at various concentrations (25, 50, 100, 200, 300 µg/ml), and cultured under 5% $CO_2$ at 37° C. At this time, control treated with medium alone was also prepared and used for experiment. After 24 hours, an MTT solution was added to culture for 1 hour, and then, absorbance was measured by ELISA equipment.

Figure 4A:
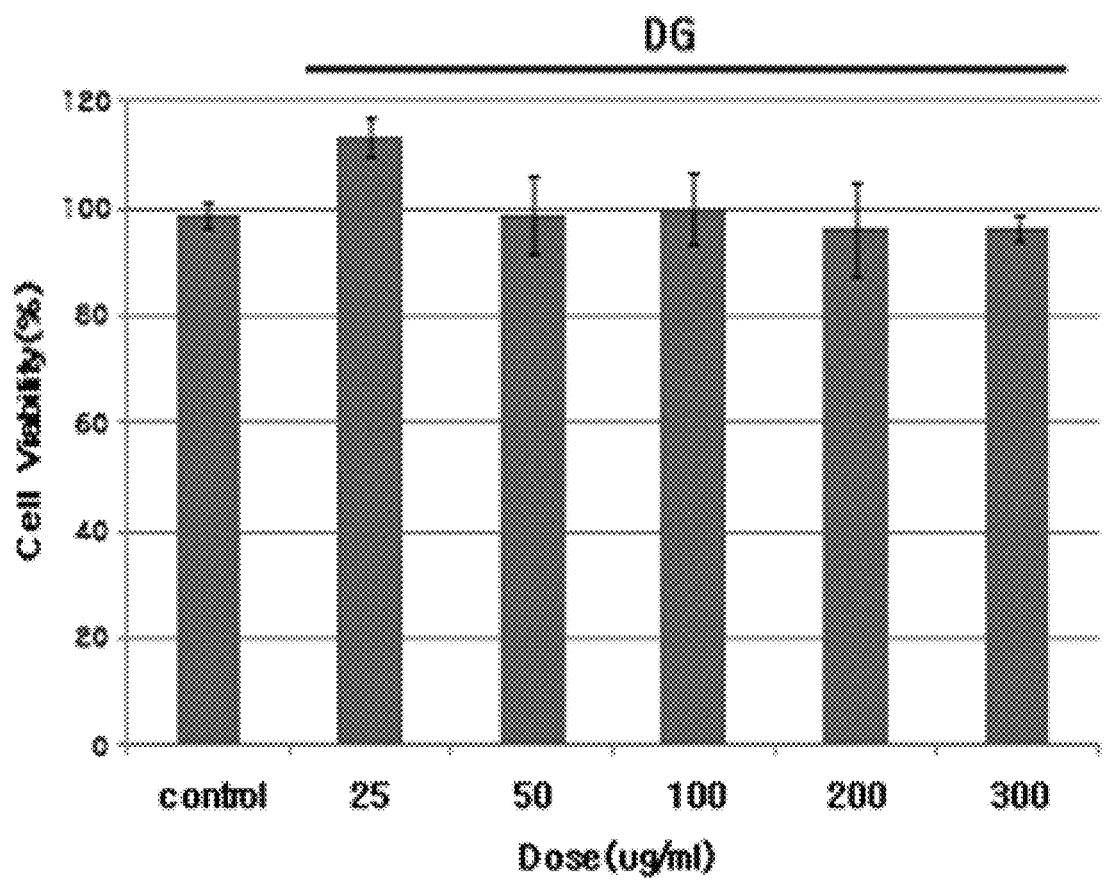
FIG. 4a shows the results of measurements of the effects of combined extract (DG) on cell viability.

As explained, cell viability of each group was obtained by measuring MTT reduction degree, and the results are shown in FIG. 4a.

As shown in FIG. 4a, it can be seen that since the combined extract of the present invention has no toxicity even if taken in a large amount, it may be safely used as an active ingredient of a pharmaceutical composition or a food composition.

Meanwhile, as according to the results of acute toxicity test using ICR mouse (5-week age), the combined extract (DG) of the present invention did not show toxicity until concentration of 2 g/kg/10 ml (oral administration) (results not described).

<1-2> Effect of Combined Extract (MYH) on Brain Cell Death

For MTT analysis, cultured SH-SY5Y cells were treated with the combined extract (MYH) prepared in <Example 1-3> at various concentrations (6.25, 12.5, 25, 50 µg/ml), and cultured under 5% $CO_2$ at 37° C. At this time, control treated with medium alone was also prepared and used for experiment. After 24 hours, an MTT solution was added to culture for 1 hour, and then, absorbance was measured by ELISA equipment.

Figure 4B:
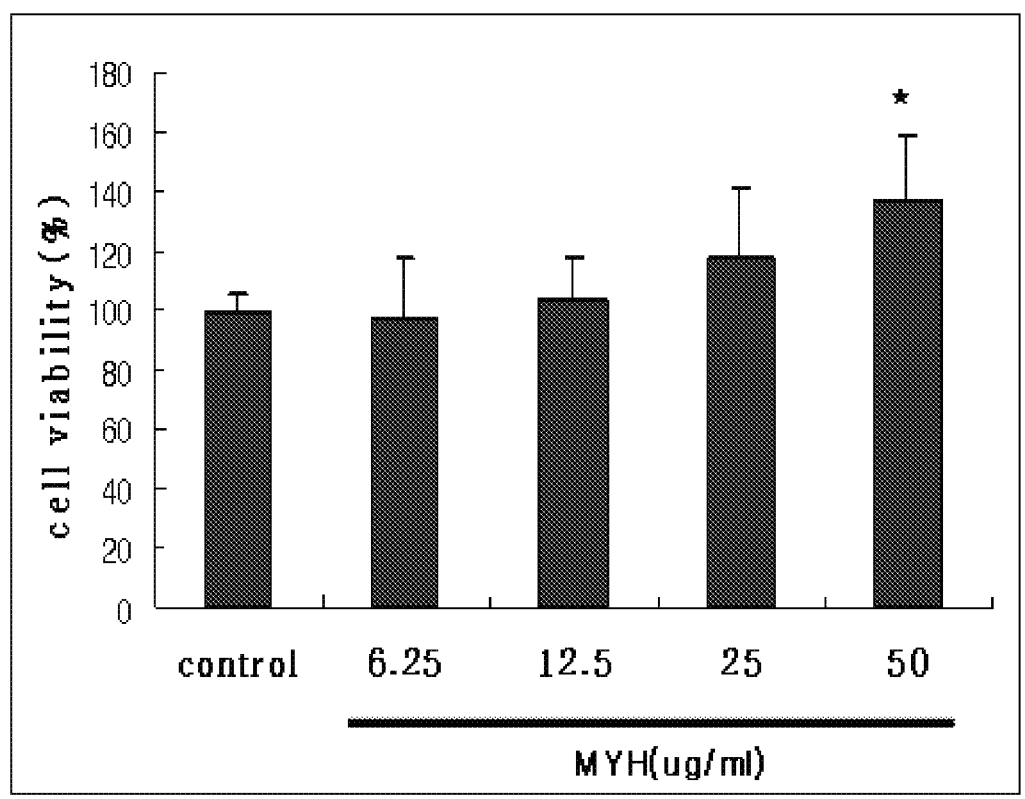
FIG. 4b shows the results of the measurements of the effects of combined extract (MYH) on cell viability.

As explained, cell viability of each group was obtained by measuring MTT reduction degree, and the results are shown in FIG. 4b.

As shown in FIG. 4b, it can be seen that since the combined extract of the present invention has no toxicity even if taken in a large amount, it may be safely used as an active ingredient of a pharmaceutical composition or a food composition.

What is claimed is:

1. A method for treating Parkinson's disease in a patient in need thereof comprising administering to the patient a composition comprising effective amounts of a Longan arillus extract, a Polygalae radix extract and an Angelicae tenuissumae radix extract,
   wherein the extracts are obtained using at least one solvent selected from the group consisting of water, ethanol, propanol, and butanol.

2. The method according to claim 1, wherein the extract combination further comprises at least one extract selected from the group consisting of Puerariae radix extract, Scutellaria radix extract, Platycodi radix extract, Angelicae Dahuricae radix extract, Cimicifugae Rhizoma extract, Raphani Semen extract, and Acorus Gramineri Rhizoma extract.

3. The method according to claim 2, wherein the composition comprises the extracts in the following amounts: 15-20 parts by weight of Longan arillus, 10 to 15 parts by weight of Angelicae tenuissimae radix, 10 to 15 parts by weight of Polygalae radix, 15 to 20 parts by weight of Puerariae radix, 5 to 10 parts by weight of Scutellaria radix, 1 to 5 parts by weight of Platycodi radix, 5 to 10 parts by weight of Angelicae Dahuricae radix, 5 to 10 parts by weight of Cimicifugae Rhizoma, 5 to 10parts by weight of Raphani Semen and 15 to 20 parts by weight of Acorus Gramineri Rhizoma.

4. The method according to claim 2, wherein each of the at least one extract is obtained using at least one extraction solvent selected from the group consisting of water, at least one organic solvent selected from C1-4 lower alcohol, hexane, methylene chloride, acetonitrile and acetone, and a mixed solvent thereof.

\* \* \* \* \*